US006911318B2

(12) United States Patent
Kahne

(10) Patent No.: US 6,911,318 B2
(45) Date of Patent: Jun. 28, 2005

(54) BACTERIAL TRANSGLYCOSYLASES: ASSAYS FOR MONITORING THE ACTIVITY USING LIPID II SUBSTRATE ANALOGS AND METHODS FOR DISCOVERING NEW ANTIBIOTICS

(75) Inventor: Suzanne Walker Kahne, Princeton, NJ (US)

(73) Assignee: The Trustees of Princeton University, Princeton, NJ (US)

( * ) Notice: Subject to any disclaimer, the term of this patent is extended or adjusted under 35 U.S.C. 154(b) by 211 days.

(21) Appl. No.: 10/263,302

(22) Filed: Oct. 2, 2002

(65) Prior Publication Data
US 2003/0129683 A1 Jul. 10, 2003

Related U.S. Application Data

(63) Continuation of application No. 09/518,080, filed on Mar. 3, 2000, now Pat. No. 6,461,829.
(60) Provisional application No. 60/122,966, filed on Mar. 3, 1999, and provisional application No. 60/137,696, filed on Jun. 4, 1999.

(51) Int. Cl.[7] ............................. C12Q 1/48; C12Q 1/44; C12Q 1/37; C12Q 1/00
(52) U.S. Cl. ............................ 435/15; 435/19; 435/23; 435/24; 435/7.71; 435/4
(58) Field of Search ............................ 435/15, 19, 23, 435/24, 7.71, 4

(56) References Cited

U.S. PATENT DOCUMENTS

| 3,949,070 A | 4/1976 | Arai et al. .................. 424/118 |
| 4,011,140 A | 3/1977 | Komatsu ..................... 195/80 |
| 6,461,829 B1 * | 10/2002 | Kahne ......................... 435/15 |

FOREIGN PATENT DOCUMENTS

| EP | 1 159 293 A1 | 3/2000 |
| WO | WO 94/10340 | 5/1994 |
| WO | WO 99/38958 | 8/1999 |
| WO | WO 2001/12132 A1 | 8/2000 |

OTHER PUBLICATIONS

Fan, C. et al., *Science*, 1994, 266, 439.
Benson, T.E. et al., *Natl. Struct. Biol.*, 1995, 2, 644.
Jin, H.Y. et al., *Biochemistry*, 1996, 35, 1423.
Skarzynski, T. et al., *Structure*, 1996, 4, 1465.
Schonbrunn, E. et al., *Structure*, 1996, 4, 1065.
Benson, T.E. et al., *Biochemistry*, 1997, 36, 806.
Gittins, J.R. et al., *FEMS Microbiol. Rev.*, 1994, 13, 1.
Bupp, K. et al., *Bacteriol*, 1993, 175, 1841.
Pless, D.D. et al., *J. Biol. Chem*, 1973, 248, 1568.
Men, H. et al., *J. Amer Chem Soc*, 1998, 120, 2485.
Nakagawa, J., et al., *J. Biol. Chem*, 1984, 259, 13937.
Spratt, B.G. et al., *Mol. Microbial*, 1996, 19, 639.
Vollmer, W., *J. Biol. Chem.*, 1999, 279, 6726.
Van Heijenoort, Y. et al., *FEBS Lett.*, 1978, 89, 141.
Di Giulmi, A.M. et al., *J. Bacteriol*, 1998, 180, 5652.

(Continued)

*Primary Examiner*—Louise N. Leary
(74) *Attorney, Agent, or Firm*—Woodcock Washburn LLP

(57) ABSTRACT

This invention provides a direct method for monitoring bacterial transglycosylase activity using labeled substrates produced by chemo-enzymatic synthesis wherein the labels are selected to permit the detection of both polymeric and non-polymeric products simultaneously, either directly or following the separation of product from starting material. The invention promotes the discovery of new antibiotics with activity against bacterial transglycosylases by a) laying the groundwork for structural analysis of purified, active transglycosylase (which permits structure-based design); and b) providing an assay that can be used to screen for inhibitors.

16 Claims, 13 Drawing Sheets

OTHER PUBLICATIONS

Brotz, H. et al., *Mol Microbiol,* 1998, 30, 317.
Esteve–Garcia, E. et al., *Poult Sci,* 1997, 76, 1728.
Brotz, H. et al., *Mol Microbiol,* 1998, 30, 317.
Esteve–Garcia, E. et al., *Poult Sci,* 1997, 76, 1728.
Brotz, H. et al., *Eur J Biochem,* 1997, 246, 193.
Pan, Y.T. et al., *Arch Biochem Biophys,* 335, 258.
Mohan, B. et al., *Br Poult Sci.,* 1996, 37, 395.
Izat, A.L. et al., *Poult Sci.,* 1990, 69, 1787.
Salmon, R.E. et al., *Poult Sci.,* 1990, 69, 1787.
Jiraphocakul, S. et al., *Poult Sci.,* 1990, 69, 1966.
Zotchev, S.B. et al., *Dokl Akad SSSR,* 1990, 313, 203.
Mani, N. et al., *J. Antibot(Tokyo),* 1998, 51, 471.
Mani, N. et al., *J. Antibot(Tokyo),* 1998, 607, 11.
van Heijenoort, Y. et al., *J. Bacteriol,* 1992, 174, 3549.
van Heijenoort, Y. et al., *J. Bacteriol,* 1992, 174, 6004.
Yveline van Hiejenoort, et al., "Membrane Intermediates in the Peptidoglycan Metabolism, of *Escherichia coli*: Possible Roles of PBP 1b and PBP 3", *Journal of Bacteriology,* 1992, 174(11), 3549–3557.
Heike Brotz, et al., "The Lantibiotic Mersacidin Inhibits Peptidoglycan Synthesis by Targeting Lipid II", *Antimicrobial Agents and Chemotheraphy,* 1998, 42(1), 154–160.
Genevieve Auger, et al., "Synthesis of an analogue of the lipoglycopeptide membrane intermediate I of peptidoglycan biosynthesis", *Letters in Peptide Science,* 1997, 4, 371–376.
Hongbin Men, et al., "Substrate Synthesis and Activity Assay for MurG", *J. Am. Chem. Soc.,* 1998, 120(10), 2484–2485.

\* cited by examiner

No reliable assays for bacterial transglycosylases

C55 lipid-linked substrate        polymeric substrate

Chemo-enzymatic synthesis of soluble transglycosylase substrates

Synthesis and Purification of Biotinylated
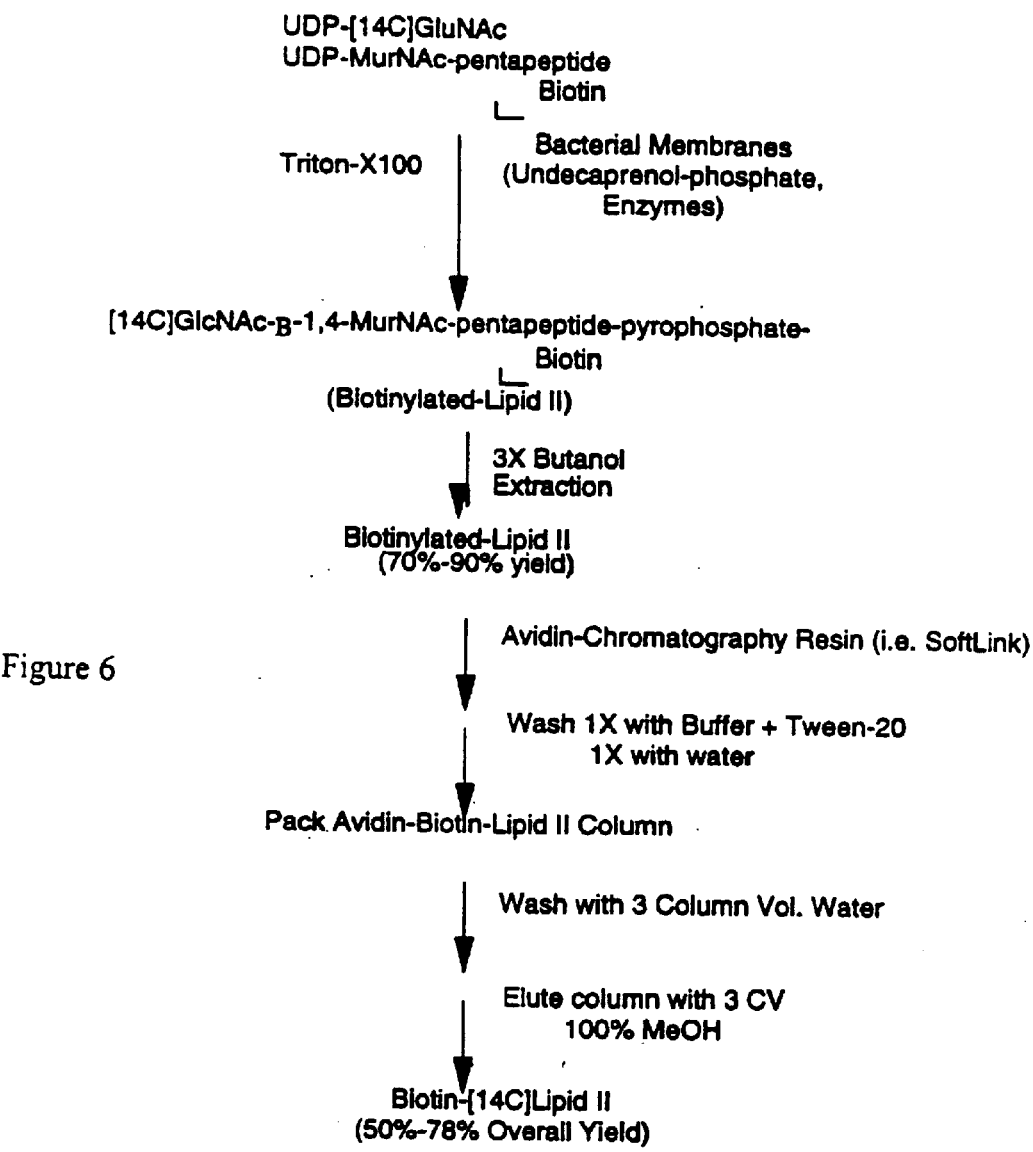
Figure 6
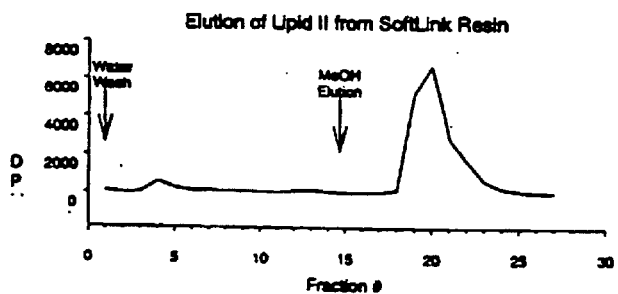

Ramoplanin (factor A2)

BACTERIAL TRANSGLYCOSYLASES: ASSAYS FOR MONITORING THE ACTIVITY USING LIPID II SUBSTRATE ANALOGS AND METHODS FOR DISCOVERING NEW ANTIBIOTICS

This application is a continuation of application Ser. No. 09/518,080, filed Mar. 3, 2000 now U.S. Pat. No. 6,461,829 which claims benefit under 35 U.S.C. §119(e) to U.S. provisional application Ser. No. 60/122,966 filed Mar. 3, 1999 and U.S. provisional application Ser. No. 60/137,696 filed Jun. 4, 1999. The disclosure of each of the foregoing is hereby incorporated by reference in its entirety.

1. FIELD OF THE INVENTION

The invention generally applies to an assay for monitoring bacterial transglycosylase activity and a method for discovering compounds like antibiotics that inhibit bacterial transglycosylases by screening compounds of interest for their ability to inhibit the formation of NAG-NAM (N-acetylglucosamine-N-acetylmuramic acid or GlcNAc-MurNAc) dimers and higher order polymers using said assay.

2. BACKGROUND OF THE INVENTION

2.1. Bacterial Enzymology

The emergence of resistance to existing antibiotics has rejuvenated interest in bacterial enzymology. It is hoped that detailed mechanistic and structural information about bacterial enzymes involved in critical biosynthetic pathways could lead to the development of new antibacterial agents. Some of the best antibiotics function by interfering with the biosynthesis of the peptidoglycan polymer that surrounds bacterial-cells. Because interference with peptidoglycan biosynthesis is a proven strategy for treating bacterial infections, all of the enzymes involved in peptidoglycan biosynthesis are potential targets for the development of new antibiotics. Although remarkable progress has been made in characterizing some of the early enzymes in the biosynthetic pathway (See, e.g., Fan, C. et al. Science 1994, 266, 439; Benson, T. E. et al. Nat. Struct. Biol. 1995, 2, 644; Jin, H. Y. et al. Biochemistry 1996, 35, 1423; Skarzynski, T. et al. Structure 1996, 4, 1465; Schonbrunn, E. et al. Structure 1996, 4, 1065; Benson, T. E. et al. Biochemistry 1997, 36, 806), the downstream enzymes have proven exceedingly difficult to study.

There are two main reasons for this difficulty: First, the downstream enzymes are membrane-associated, making them intrinsically hard to handle (See, e.g., Gittins, J. R. et al. FEMS Microbiol. Rev. 1994, 13, 1; Bupp, K. and van Heijenoort, J. J. Bacteriol. 1993, 175, 1841.); second, discrete substrates for most of the downstream enzymes are either not available or not readily so (See, e.g., Pless, D. D. and Neuhaus, F. C. J. Biol. Chem. 1973, 248, 1568; van Heijenoort, Y. et al. J. Bacteriol. 1992, 174, 3549.).

For example, the Lipid II substrate is difficult to obtain in large quantities from natural sources and difficult to handle due to its detergent like properties. In the absence of readily available, well-behaved discrete substrates, it has been impossible to develop enzyme assays that can be used to measure the activity of the downstream enzymes reliably and under a well-defined set of reaction conditions. This unfulfilled need has thwarted attempts to purify many of the downstream enzymes in an active form suitable for structural characterization and attempts to obtain detailed mechanistic information on such enzymes. It has also complicated screening for inhibitors. The use of synthetic or semi-synthetic substrate analogs with characteristics that make them easier to handle than the natural substrates and/or facilitate product detection could permit the study of many downstream enzymes (Men, H. et al. J. Amer Chem Soc 1998, 120, 2485 and PCT publication WO 99/38958).

2.2 Peptidoglycan Biosynthesis

FIG. 1 illustrates the key pathways for biosynthesis of peptidoglycan. Lipid I is converted to Lipid II by the enzyme MurG (N-acetylglucosaminyltransferase). Several reactions occur downstream from the MurG-catalyzed reaction. After translocation, Lipid II is either conjugated to another Lipid II or to an existing peptidoglycan by the enzyme transglycosylase. Cross-linking of peptides of spatially adjacent peptidoglycan molecules is accomplished by the enzyme transpeptidase.

2.3. Transglycosylases

FIG. 2 illustrates one family of downstream enzymes, the transglycosylases, which are involved in the late steps of peptidoglycan biosynthesis. Transglycosylases catalyze an extracellular step in the biosynthetic pathway of peptidoglycan biosynthesis, i.e., the coupling of two Lipid II molecules, coupling of two Lipid II analogs, or the coupling of one Lipid II molecule to the C4 hydroxyl of an N-acetylglucosaminyl acceptor that is part of the growing peptidoglycan polymer.

FIG. 3 illustrates the cellular location of the key enzymes of peptidoglycan biosynthesis. In the cytoplasm MurG acts to form Lipid I and transglycosylase acts to form Lipid H. The transglycosylase and transpeptidase reactions occur extracellularly, at the bacterial membrane surface.

There are multiple different transglycosylases in bacterial cells. Both bifunctional and monofunctional enzymes have been identified (Nakagawa, J. et al. J. Biol. Chem., 1984, 259, 13937; Spratt, B. G. et al. Mol. Microbiol., 1996, 19, 639). The bifunctional enzymes also contain transpeptidase activity which is sensitive to penicillin. The bifunctional enzymes are most commonly known as penicillin binding proteins (PBPs). The transglycosylase domains of some PBPs are believed to be functional in the absence of other proteins (Vollmer, W. J. Biol. Chem. 1999, 279, 6726). The transglycosylase domains of other PBPs are believed to be dependent on the presence of other proteins that have been implicated in bacterial cell growth or cell division (Vollmer, ibid). It is known that inhibition of transglycosylase activities, e.g., by treatment with moenomycin, leads to bacterial cell death. Moenomycin besides being known as antibiotic is also as an antitumor drug, see for example incorporated by reference U.S. Pat. No. 4,011,140. Antibiotics are also important in food industry as growth-promoting agents for plants and domestic animals, e.g., U.S. Pat. No. 3,949,070 discloses pholipomycin for such an application. Hence, the instant transglycosylase assay is an important tool for identifying antibiotics and other classes of drugs like antitumor drugs, antiviral drugs, growth promoters, etc. Unfortunately, there is only one membrane-free assay for transglycosylase activity. This assay involves the isolation of [$^{14}$C]-radiolabeled Lipid II from bacterial cells or bacterial membrane preparations supplemented with appropriate starting materials (van Heijenoort, Y. et al. FEBS Lett., 1978, 89, 141). The isolated Lipid II is then treated with a crude or a partially purified preparation of a PBP and the formation of polymer is detected by the appearance of radioactivity at the baseline of a paper chromatogram or by retention of radioactivity on a filter. This assay has severe limitations. The major one is that it has only been shown to work for a membrane bound form of PBP1b of *E. coli* origin (Di Giulmi, A. M. et al. J. Bacteriol 1998, 180, 5652). In addition, the Lipid II substrate is difficult to isolate in significant quantities and the assay can be hard to reproduce due to problems handling the substrate, which contains a 55-carbon lipid chain.

FIG. 4 illustrates some of the difficulties in isolating and handling Lipid II, and the problems in detecting the formation of products smaller than polymers. These problems have prevented the development of simple, direct assays for transglycosylase activity that work for both soluble and membrane-bound transglycosylase domains. Consequently, it has not been possible to demonstrate activity in transglycosylase domains that have been engineered for solubility or to purify any transglycosylase domain to homogeneity in a quantifiably active form or to determine the minimal functional length of the transglycosylase domain; nor has it been possible to carry out any detailed mechanistic studies, or to determine the substrate requirements.

Development of reliable, direct assays for monitoring transglycosylase activity that facilitates the detection of products of any length would promote the development of new antibiotics by: a) permitting the purification of active transglycosylase domains suitable for structural and mechanistic investigations; and b) providing a screen for compounds that inhibit transglycosylase activity. There are no direct assays for monitoring transglycosylase activity that utilize synthetic substrate analogs with solubility properties that differ from the natural substrates (which contain very long lipid chains and are not soluble in water). Furthermore, there are no direct assays for monitoring transglycosylase activities that are capable of detecting non-polymeric products. Finally, there are no direct assays for monitoring transglycosylase activities that make use of purified Lipid II or Lipid I substrate analogs which further contain a fluorophore, chromophore, luminophore, or affinity label (e.g., lectin) to facilitate detection of product.

Previous assays for bacterial transglycosylase activity required radiolabeling and purification of the endogenous Lipid II substrate, N-acetylglucosamine-β-1,4-MurNAc-pentapeptide-pyrophosphoryl-undecaprenol (Brotz, H. et al. Mol Microbiol., 1998, 30, 317; Esteve-Garcia, E. et al. Poult Sci., 1997, 76, 1728; Brotz, H. et al. Eur J Biochem., 1997, 246, 193; Pan, Y. T. and Elbein, A. D. Arch Biochem Biophys., 1996, 335. 258: Mohan, B. et al. Br Poult Sci., 1996, 37, 395; Izat, A. L. et al. Poult Sci., 1990, 69, 1787: Salmon, R. E. and Stevens, V. I. Poult Sci., 1990, 69, 1133; Jiraphocakul, S. et al. Poult Sci. 1990, 69, 1966; Zotchev, S. B. et al. Dokl Akad Nauk SSSR., 1990, 313, 203; Mani, N. et al. J Antibiot (Tokyo), 1998, 51, 471; Mani, N. et al. J Antibiot (Tokyo) 1998, 607, 11; van Heijenoort, Y. et al. J Bacteriol., 1992, 174, 3549; van Heijenoort, Y. et al. J Bacteriol, 1992, 174, 6004). These methodologies involve multiple purification steps, yield limited amounts of Lipid II, and require radiolabel for detection of transglycosylase product. In addition, because of the insoluble nature of the Lipid II substrate in an aqueous milieu, irreproducible activity is also a problem. Separation of product from substrate in those methods is performed by paper chromatography or trapping product on filters.

Therefore, there exists a need for direct and simple enzyme assays that can be used both for effective screening of enzyme inhibitors and for the purification, characterization and identification of transglycosylase, its various mutants and active fragments thereof.

3. SUMMARY OF THE INVENTION

Substrate analogs of Lipids I and/or II are disclosed having (i) a structure that is accepted by at least one wild type transglycosylase enzyme, and (ii) structural features that either facilitate the separation of labeled Lipid II from the labeled coupling product or that facilitate the detection of coupled products.

More generally, the substrate may have the formula I:

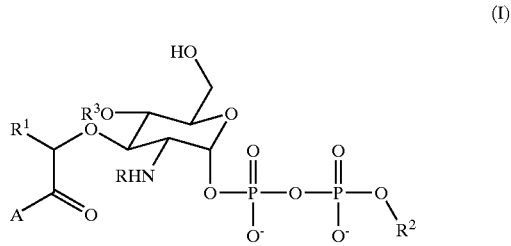

(I)

in which "R" is an acyl group comprising 2 or more carbon atoms. "$R^1$" is a substituted or unsubstituted alkyl, alkynyl, aryl, arylalkyl, heteroaryl, heteroaralkyl, heterocycloalkyl, trialkylsilyl, alkaryl or cycloalkyl group comprising 1 or more carbon atoms. "$R^2$" is a substituted or unsubstituted alkyl, alkynyl, aryl, arylalkyl, heteroaryl, heteroaralkyl, heterocycloalkyl, trialkylsilyl, alkaryl or cycloalkyl group comprising 5 or more carbon atoms. Heterocycle can be furyl, thienyl, imidazolyl, indolyl, pyridinyl, thiadiazolyl, thiazolyl, piperazinyl, dibenzfuranyl, dibenzthienyl, pyrimidinyl, or pyridazinyl. "$R^3$" is a glucosaminyl group comprising 5 or more carbon atoms or when $R^3$ is not a glucosaminyl group it can be absent or replaced by hydroxyl, oxo, bromo, fluoro, chloro, iodo, mercapto, cyano, alkylthio, carboxyl, alkoxycarbonyl, alkenyl, nitro, amino, alkoxyl, carboxamido, isothioureido, amidino, guanidino or any other suitable group; "A" is generally a substituted or unsubstituted amino acid residue or a peptide comprising 2 or more substituted or unsubstituted amino acid residues, said substance exhibiting a binding affinity for at least wild type transglycosylase enzyme. "A" can be also absent. Substitutions may comprise one or more of halo, alkyl, hydroxy, alkoxy, phenoxy, $CF_3$, amino, alkylamino, dialkylamino, —COOR or —$NO_2$. Without being bound by the theory any of Rs' or A can be absent. In a specific embodiment, the substance of the invention is not the unmodified Lipid II, the natural substrate of wild type transglycosylase enzyme. That is, in a specific embodiment, the substance of the invention, whether it is Lipid I precursor or Lipid II as final substrate, at least one of them must be somehow different from naturally occurring counterparts. Specifically, a labeled Lipid II derived from a process disclosed for example in commonly owned WO 99/38958 is clearly different from the natural substrate and can be used in a method of the present invention.

The substance of formula I is useful for screening, in assays, and other analytical means of defining transglycosylase activity, means of inhibition, and substrates.

While the preferred sugar nucleus of the invention comprises N-acetylglucosamine other examples of monosaccharide units can be in either D and L configurations and can be aldose, erythrose, threose, ribose, arabinose, xylose, lyxose, allose, altrose, glucose, mannose, gulose, idose, galactose and talose and ketoses like dihydroxyacetone, erythrulose, ribulose, xylulose, puscose, fructose, sorbose and/or tagatose. The naturally-occurring monosaccharide units also include those monosaccharides which represent naturally-occurring substitutions. Preferably these are deoxy sugars, fucose, rhamnose, digitoxose, preferably deoxyamino sugars such as, for example, glucosamine, mannosamine, galactosamine, aldonic, aldaric and/or uronic acids such as, for example, gluconic acid or glucuronic acid, and more preferably deoxyacylamino sugars such as, for example, N-acetylglucosamine, N-acetylmuramine, N-acetylmannosamine, or N-acetylgalactosamine. It also is suitable to use amino acid-carrying monosaccharides and monosaccharides which carry lipid, phosphatidyl or polyol residues.

The oligopeptide can contain D or L amino acid residues and the amino acids can be joined at α carboxyl groups or at γ carboxyl groups, and at α amino groups or at ε amino groups, or at combinations of these linkages. Furthermore the "A" and "$R^1$" groups can independently comprise labels, including radioisotopes, chromophores, and fluorophores and can also independently comprise binding ligands including, but not limited to, biotin, which has affinity to avidin. Other binding pairs are easily imaginable, e.g., protein G-Ig or immunoglobulin, protein A-Ig, biotin-streptavidin, biotin-neutravidin, antigen-antibody, lectin-glycoprotein, and alike.

Thus, novel compositions and methods of analysis are disclosed for measurement of a key step in peptidoglycan synthesis. These compositions and methods should be useful in searching and/or studying new or existing drugs like antibiotics. In one embodiment a method of discovering an inhibitor of transglycosylase activity is provided, which comprises contacting a substance suspected of having transglycosylase inhibitory activity with an enzyme exhibiting transglycosylase activity in the presence of a substrate therefor, which substrate comprises at least one feature that facilitates the detection or measurement of a coupling product formed from the coupling of the substrate and an acceptor moiety, measuring the amount of coupling product formed, and comparing this amount with that measured in the absence of said substance. Another embodiment is a method for screening antibiotics is provided, which comprises contacting a sample or serial dilutions of the sample suspected of having antibiotic activity with a substance of formula I, which substance will have a feature that facilitates the detection or measurement of a product formed by coupling of at least two molecules of this substance and, measuring the amount of coupled product formed, and comparing this amount with that measured in the absence of said suspected sample. Discovered antibiotics will be useful as antibacterial, antitumor, antiviral, and/or immunomodulating drugs, which may act upon directly upon transglycosylase or by preventing coupling of the substance of formula I. Feature necessary for coupling detection can include labels like florescent or lumiscent labels, radioisotopes, enzymes, lectins, or any other art-known means of detection.

These and other advantages of the present invention are disclosed in more detail in the following detailed description of the invention. Clearly, a variety of applications for this invention can be imagined and as disclosed hereinafter the examples are not in any way limiting but serve only for the purpose to illustrate these and many other possible applications.

4. BRIEF DESCRIPTION OF THE DRAWINGS

FIG. 6 illustrates the attachment and synthesis of biotinylated Lipid II (top) and an elution pattern of Lipid II from SoftLink Resin (bottom).

5. DETAILED DESCRIPTION OF THE PREFERRED EMBODIMENTS

5.1. General Aspects of the Invention

Figure 1:
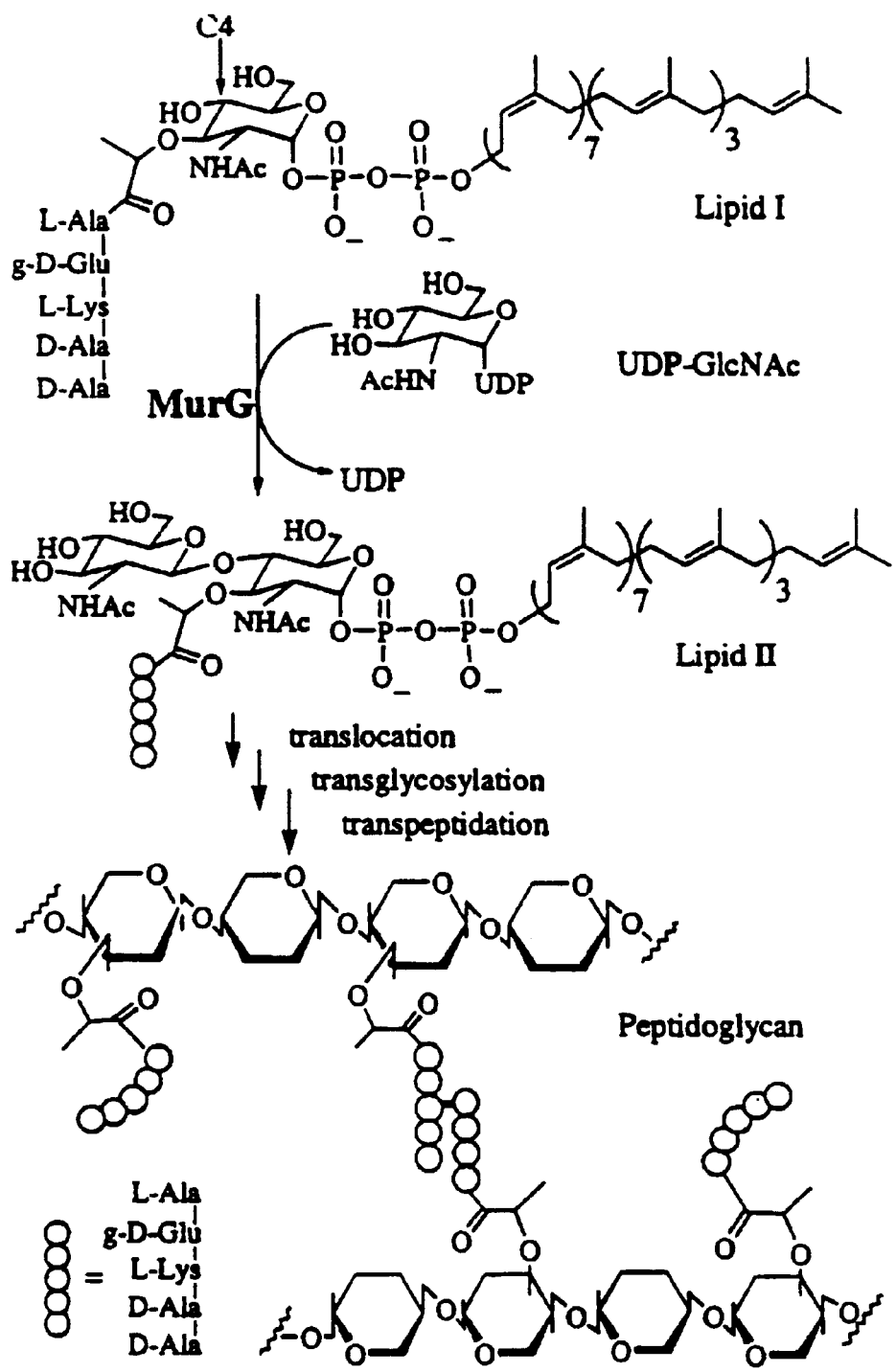
FIG. 1 illustrates the reaction catalyzed by the enzymes of peptidoglycan biosynthesis.
Figure 2:
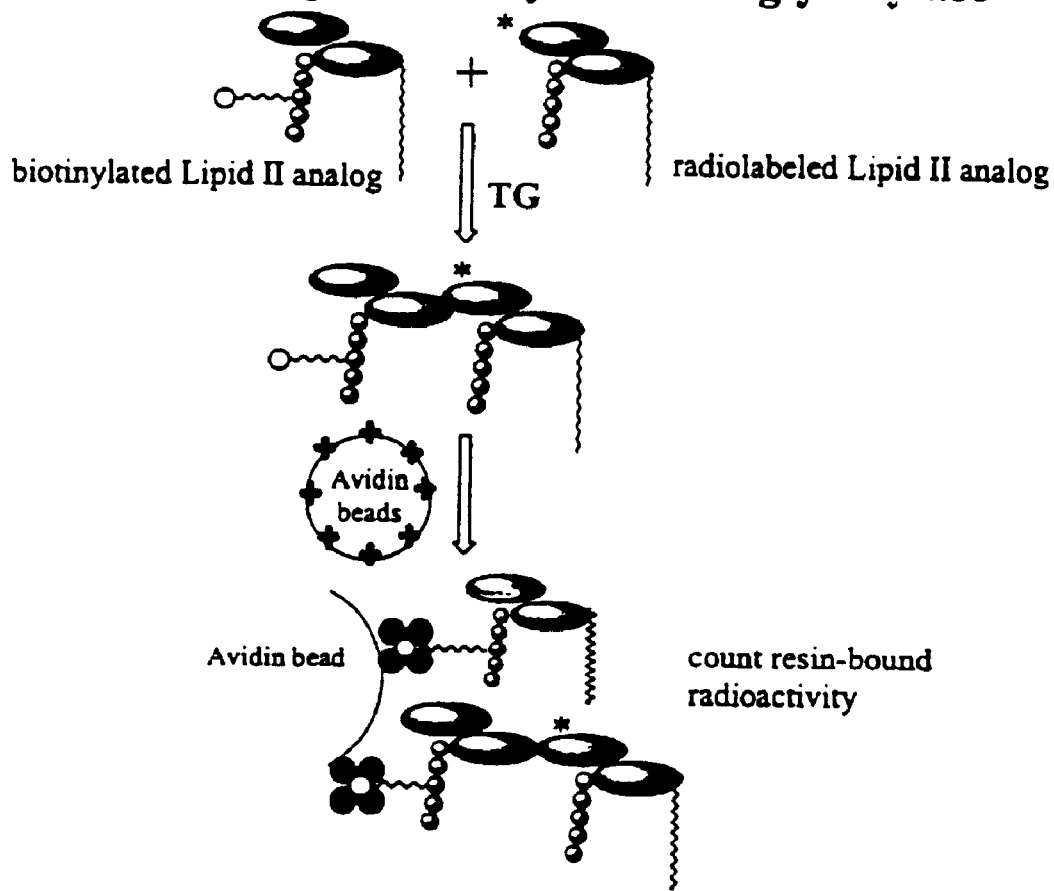
FIG. 2 illustrates the biotin capture assay for transglycosylase.
Figure 3:
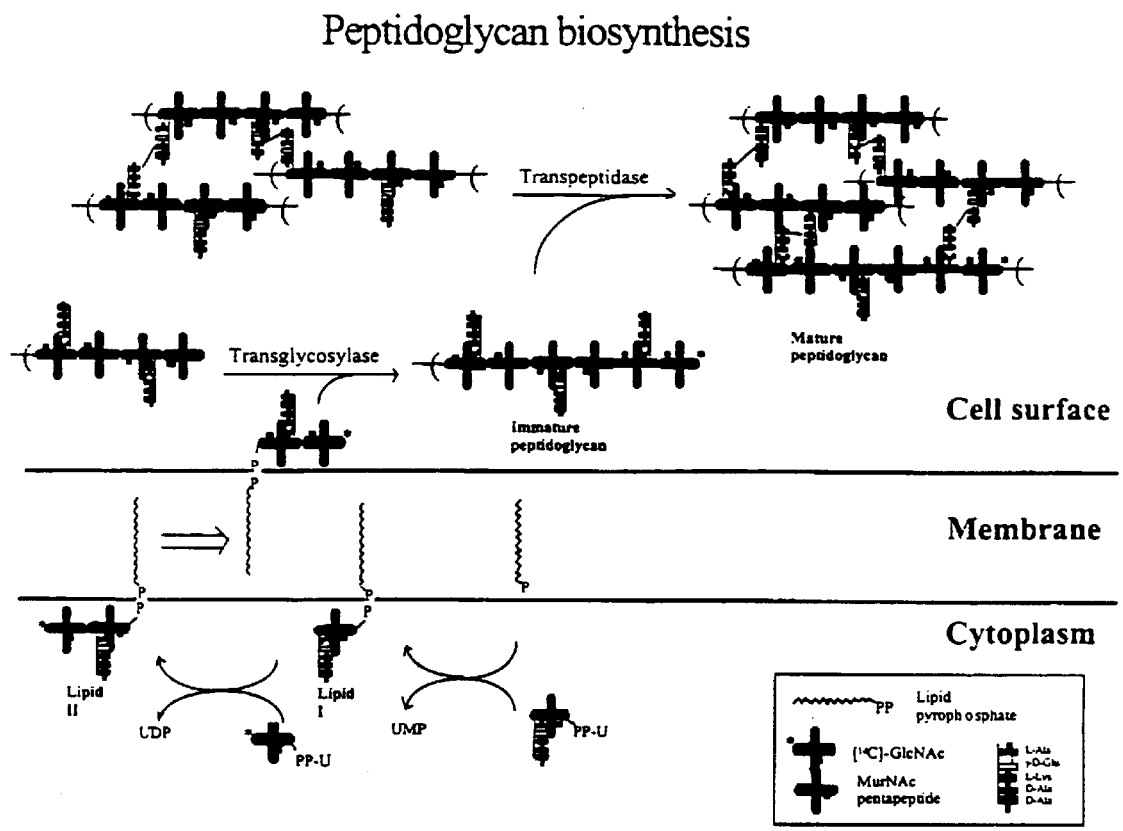
FIG. 3 illustrates the cellular location of peptidoglycan biosynthesis.
Figure 4:
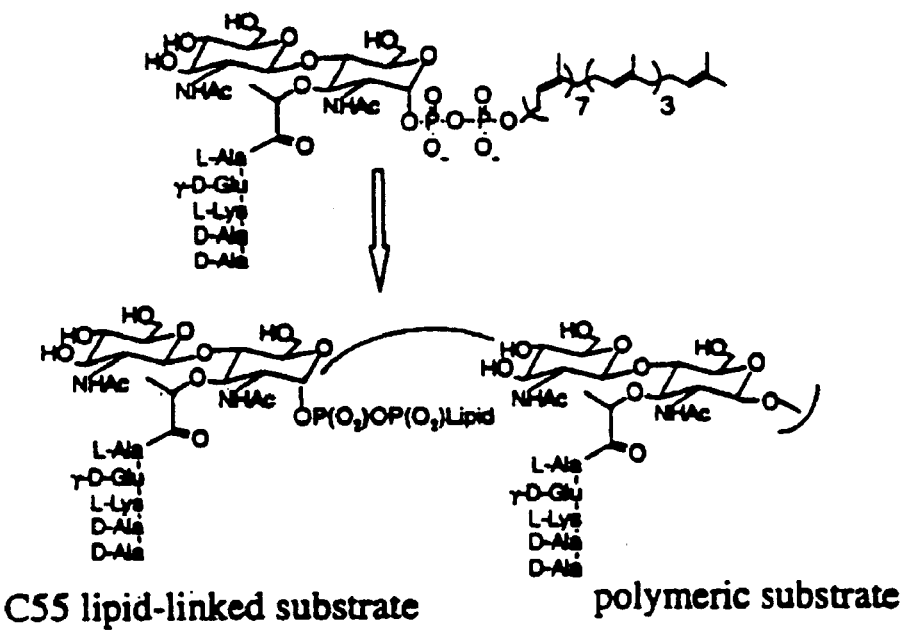
FIG. 4 illustrates the bacterial transglycolase reaction.
Figure 5:
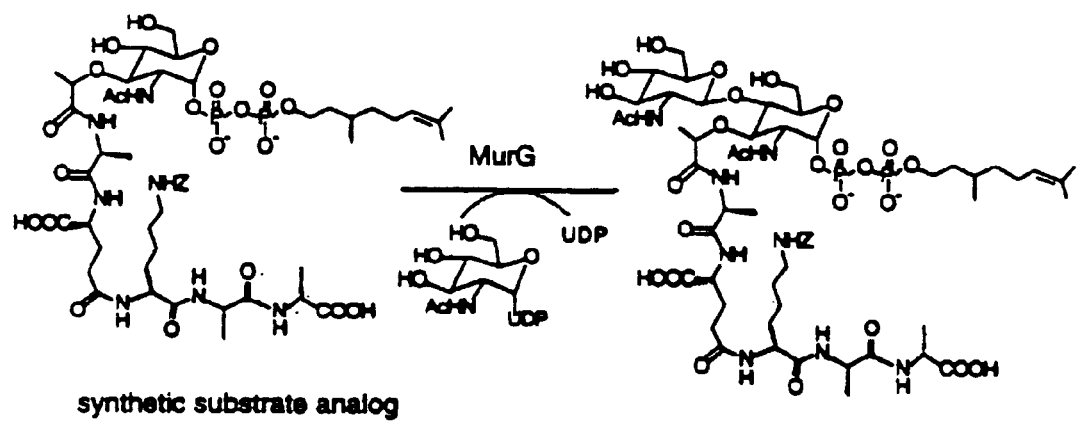
FIG. 5 illustrates chemo-enzymatic synthesis of soluble transglycosylase substrates.

It should be evident to one of ordinary skill that the substance disclosed and described herein can also possess inhibitory activity against the transglycosylation activity of at least wild type transglycosylase enzyme, its homologs, recombinant or natural, and, possibly, certain mutant forms thereof, depending in part on the strength of its binding affinity with the protein or its active fragments. That is, a substrate analog of the present invention, by binding tenaciously to the protein or active fragment thereof, can potentially inhibit the ability of transglycosylase or a transglycosylase-like enzyme to catalyze the transglycosylation. Of course, transglycosylase and its homologs are derived from *E. coli, H. influenzae* and other gram-negative bacteria. Gram-positive bacteria, such as *B. subtilis, E. faecalis, E. hirae*, as well as *M. tuberculosis*, are also known to harbor homologs of transglycosylase.

5.2. The Transglycosylase Reaction

The transglycosylase joins the Lipid II analogs to form a labeled coupling product consisting of at least two NAG-NAM disaccharides that may be identically or differentially labeled. Thus, the substrate may have the structure in which "R" in formula I represents an acetyl group ($CH^3CO$—) and $R^2$ represents a citronellol moiety or other suitable moiety like hydroxycitronellal; methyl anthranilate; hydroxycitronellal; indol; phenyl acetaldehyde; 4-(4-hydroxy4-methylpentyl)-3-cyclohexene-1-carboxaldehyde; geraniol; geranyl acetate; linalool; linalyl acetate; tetrahydrolinalool; citronellol; citronellyl acetate; dihydromyrcenol; dihydromyrcenyl acetate; tetrahydromyrcenol; terpinyl acetate; nopol; nopyl acetate; linalool; nerol; alpha-terpineol; linalool oxide; hydroxylinaool; phenyl ethyl alcohol; ethylphenol; benzylalcohol; 3-hydroxydamascone; or 3-oxo-alpha-ionol; or vinylagaicol. R2 can also be saturated and unsaturated alkenes such as isoprene units, butadiene, styrene and alike. Any olefin containing a hydrogen atom on a carbon atom adjacent to a double bond may be used in the process of the present invention. The simplest such olefin will contain three carbon atoms. The olefinically unsaturated compound may be an aliphatic, cycloaliphatic, or alkylaryl straight-chain or branched chain compound containing one or more double bonds. The olefinically unsaturated compound may be a hydrocarbon or a compound containing hetero-atoms in the molecule. The representative examples of saturated hydrocarbons are, for example, n-hexane, 2-methylpentane, 3-methylpentane, 2,2-dimethylbutane, 2,3-dimethylbutane, n-heptane, 2-methylhexane, 3-methylhexane, 3-ethylpentane, 2,2-dimethylpentane, 2,3-dimethylpentane, 2,4-dimethylpentane, 3,3-dimethylpentane, 2,2,3-trimethylbutane, n-octane, 2-methylheptane, 3-methylheptane, 2,2-dimethylhexane, 2,3-dimethylhexane, 2,5-dimethylhexane, 3,4-dimethylhexane, 2,2,3-trimethylpentane, 2,2,4-trimethylpentane (isooctane), 2,3,3-trimethylpentane, 2,3,4-trimethylpentane, cyclohexane, methylcyclopentane, methylcyclohexane, ethylcyclopentane, 1,1-, 1,2-, and 1,3-dimethylcyclopentane, ethylcyclohexane, 1,2-, 1,3- and 1,4-dimethylcyclohexane. isopropylcyclopentane and the like. Examples of unsaturated hydrocarbons are 1-Octene, 1-Decene, 1-Undecene, 1-Dodecene, 1-Tridecene, 1-Tetradecene, 1-Pentadecene, 1-Hexadecene, 1-Heptadecene, and 1-Octadecene.

To prepare polymers having an additional terminal functional groups, the polymer chains are preferably terminated with hydroxyl, carboxyl, phenol, epoxy, or amine groups by reaction with ethylene oxide, oxetane, 2,2-dimethyloxetane, carbon dioxide, a protected hydroxystyrene monomer, ethylene oxide plus epichlorohydrin, or the amine groups. Preferably $R^2$ represents polyisoprenoids, i.e., lipids composed of repeating isoprene units or steroids, i.e. lipids composed of isoprene units in a ring structure, e.g., cholesterol and testosterone. R2 can also be ether lipids, i.e., lipids with an alkyl (or alkenyl) group or glycolipids, i.e., lipids which contain one or more sugar residues. The isoprenoids, farnesyl pyrophosphate, geranyl pyrophosphate and like, as intermediates in the cholesterol biosynthetic pathway are derived from mevalonic acid and can be made synthetically or via biosynthetic pathway which can imitate appropriate enzymes including but not limited to 3-hydroxy-3-methyl glutaryl coenzyme A reductase, mevalonic acid kinase, mevalonate 5-pyrophosphate decarboxylase, farnesyl pyrophosphate synthase, geranylgeranyl pyrophosphate synthase, hexaprenyl pyrophosphate synthase-related protein, isopentenyl pyrophosphate isomerase, chrysanthemyl pyrophosphate synthase, s-linalool synthase, 4s-limonene synthase, 5-epi-aristolochene synthase, vetispiradiene synthase, (+)-d-cadinene synthase, squalene synthase, squalene epoxidase, oxidosqualene cyclase (cycloartenol synthase), geranylgeranyl pyrophosphate hydrogenase, abietadiene synthase, casbene synthase, ent-copalyl pyrophosphate synthase A, ent-kaurene synthase, taxadiene synthase, phytoene synthase, phytoene desaturase, z-carotene desaturase, lycopene cyclase. b-carotene hydroxylase, zeaxanthin epoxidase, or violaxanthin de-epoxidase. The products can be further derivatized to obtain for example citracetal, citral dimethyl acetal, citral diethyl acetal. geranyl benzoate, geranyl tiglate, geranyl anthranilate, farnesyl benzoate, farnesyl anthranilate, farnesyl tiglate, farnesyl acetate, arnesyl hexanoate, geranyl octanoate, or farnesyl octanoate.

The oligopeptide "A" can be a tripeptide, a tetrapeptide, or a pentapeptide, either unsubstituted or substituted with a label. The oligopeptide can include natural, rare, uncommon, or synthetic D- or L-amino acid residues, including, but not limited to, meso-diaminopimelate (meso-DAP), alpha-vinyl amino acid, or alpha-oxiranyl amino acid. In a preferred embodiment, the oligopeptide can be, but is not limited to, L-Ala-γ-D-Glu-L-Lys-D-Ala-D-Ala, which can be further derivatized. In a preferred embodiment Ala is bound to the substance of the invention via lactic acid moiety, preferably through an amide bond. Useful derivatives of the oligopeptide can include those that are labeled with a radioisotope, a fluorophore, a chromophore, a luminophore, or an affinity handle such as biotin on the ε-amino group of lysine or other free amino groups, or on the terminal carboxylate or other appropriate functional group.

The substrate according to formula I can be radiolabeled at any suitable site, including on the GlcNAc sugar. Alternatively or in addition, it can be labeled on the MurNAc sugar with a chromophore, fluorophore, or affinity handle, such as biotin or any other binding ligand. Furthermore, the GlcNAc and the MurNAc can both be radiolabeled with differing isotopes. A preferred embodiment is to attach chromophores, fluorophores, or affinity labels to the substituent attached to the lactate at the C-3 position of the MurNAc sugar. For example, the substituent, "A" in formula I, could be the natural peptide if the GlcNAc sugar is radiolabeled, or it could be the natural peptide containing a radioisotope, chromophore, fluorophore, affinity label or other group on the amino group of the lysine. Other alternative for indirect label can be a lectin, e.g. wheat germ agglutinin, that binds selectively to N-acetylglucosamine and this lectin is covalently bound to a fluorescent fluorophore like pyrene, coumarin, acridone, naphthalene, or anthracene. Wheat germ agglutinin labeled with fluorescein isothiocyanate can be purchased from Polysciences, Inc. of Warrington, Pa. Substitution of a radioisotope or light-emitting probe in a natural site of the substance should not alter the chemical properties or identity of a substance. Many fluorophores are useful, including, but not limited to fluorescein, 4,4-difluoro-4-bora-3a,4a-diaza-s-indacene (BODIPY), 3-Hydroxypyrene 5,8,10-Tri Sulfonic acid, 5-Hydroxy Tryptamine, 5-Hydroxy Tryptamine (5-HT), Acid Fuhsin, Acridine Orange, Acridine Red, Acridine Yellow, Acriflavin, AFA (Acriflavin Feulgen SITSA), Alizarin Complexon, Alizarin Red, Allophycocyanin, ACMA, Aminoactinomycin D, Aminocoumarin, Anthroyl Stearate, Astrazon Brilliant Red 4G, Astrazon Orange R, Astrazon Red 6B, Astrazon Yellow 7 GLL, Atabrine, Auramine, Aurophosphine, Aurophosphine G, BAO 9 (Bisaminophenyloxadiazole), BCECF, Berberine Sulphate, Bisbenzamide, BOBO 1, Blancophor FFG Solution, Blancophor SV, Bodipy Fl, BOPRO 1, Brilliant Sulphoflavin FF, Calcein Blue, Calcium Green, Calcofluor RW Solution, Calcofluor White, Calcophor White ABT Solution, Calcophor White Standard Solution, Cascade Blue, Cascade Yellow, Catecholamine, Chinacrine, Coriphosphine O, Coumarin-Phalloidin, CY3.1 8, CY5.1 8, CY7, Dans (1-Dimethyl Amino Naphaline 5 Sulfonic Acid), Dansa (Diamino Naphthyl Sulfonic Acid), Dansyl NH—CH3 in water. DAPI, Diamino Phenyl Oxydiazole (DAO), Dimethylamino-5-Sulfonic acid, Diphenyl Brilliant Flavine 7GFF, Dopamine, Eosin, Erythrosin ITC. Ethidium Bromide, Euchrysin, FIF (Formaldehyde Induced Fluorescence), Flazo Orange, Fluo 3, Fluorescamine, Fura-2, Genacryl Brilliant Red B, Genacryl Brilliant Yellow 10GF, Genacryl Pink 3G, Genacryl Yellow 5GF, Gloxalic Acid, Granular Blue, Haematoporphyrin, Hoechst 33258 (bound to DNA), Indo-1, Intrawhite Cf Liquid, Leucophor PAF, Leucophor SF, Leucophor WS, Lissamine Rhodamine B200 (RD200), Lucifer Yellow CH, Lucifer Yellow VS, Magdala Red, Marina Blue, Maxilon Brilliant Flavin 10 GFF, Maxilon Brilliant Flavin 8 GFF, MPS (Methyl Green Pyronine Stilbene), Mithramycin, NBD Amine, Nile Red, Nitrobenzoxadidole, Noradrenaline, Nuclear Fast Red, Nuclear Yellow, Nylosan Brilliant Flavin E8G, Oregon Green, Pacific Blue, Pararosaniline (Feulgen), Phorwite AR Solution, Phorwite BKL, Phorwite Rev, Phorwite RPA, Phosphine 3R, Phycoerythrin R, Pontochrome Blue Black, Primuline, Procion Yellow, Propidium Iodide, Pyronine, Pyronine B, Pyrozal Brilliant Flavin 7GF, Quinacrine Mustard, Rhodamine 123, Rhodamine 5 GLD, Rhodamine 6G, Rhodamine B, Rhodamine B 200, Rhodamine B Extra, Rhodamine BB, Rhodamine BG, Rhodamine WT, Rose Bengal, Serotonin, Sevron Brilliant Red 2B, Sevron Brilliant Red 4G, Sevron Brilliant Red B, Sevron Orange, Sevron Yellow L, SITS (Primuline), SITS (Stilbene Isothiosulphonic acid), Stilbene, Snarf 1, sulphO Rhodamine B Can C, Sulpho Rhodamine G Extra, Tetracycline, Texas Red, Thiazine Red R, Thioflavin S, Thioflavin TCN, Thioflavin 5, Thiolyte, Thiozol Orange, Tinopol CBS, TOTO 1, TOTO 3, True Blue, Ultralite, Uranine B, Uvitex SFC, Xylene Orange, XRITC, YO PRO 1, or combinations thereof. Other classes of dyes known as triphenylmethane dyes (and, more specifically, rosaniline dyes), acid blue 25 dyes, dansyl dyes, fluorescein dyes, or 2-methoxy-2,4-diphenyl-3(2H)-furanone ("MDPF") dyes are equally suitable.

In one embodiment, the transglycosylase reaction can be carried out using two differentially labeled substrate analogs, one of which is radiolabeled and one of which is labeled with an affinity tag. Products, in this embodiment, are detected by counting the radioactivity that associates with a solid support derivatized with a receptor for the affinity tag. As an alternative embodiment, one substrate can be derivatized with biotin and the other with a fluorophore. In that embodiment, the products are detected by fluorescence polarization. That is, the rotational freedom of the fluorophore will be restricted after incorporation into the dimer or polymer reaction product, resulting in decreased anisotropy and an increase in fluorescence polarization. In the case of a biotin affinity tag, avidin- or streptavidin-derivatized resins or membranes are suitable for the separation step, but other supports are also possible. In yet another embodiment, the transglycosylase assay can be carried out with two substrate analogs that are labeled with different fluorophores, one being an acceptor and one being a donor for fluorescent energy transfer. If the substrates are labeled with fluorophores which are donor-acceptor pairs, the reaction product can be detected using a FRET-based (fluorescent resonance energy transfer) assay that permits continuous detection of product. In this FRET-based assay the lipid lengths, $R^2$ in formula I, may be natural length or shorter than natural length. When the differentially labeled Lipid II analogs are coupled, excitation at the wavelength of the donor can result in excitation at the wavelength of the acceptor (by emission from the donor, which is now in close spatial proximity) and product formation can be detected by emission at the wavelength of the acceptor. The emission increases as the products increase. Alternatively, coupling of donor and acceptor substrates can lead to quenching of the donor, detected as a decrease in fluorescence at the emission wavelength of the donor. FRET assays have advantages in terms of expense over the radiolabeling and biotin capture assay. In addition, a FRET-based assay can be formatted to permit continuous detection of product. Technical details relating to FRET assay are found for example in incorporated by reference U.S. Pat. No. 5,741,657. Useful pairs of fluorophores for FRET-based assays include, but are not limited to, fluorescein as donor with tetramethylrhodamine as acceptor, 5-((2-[(iodoacetyl) amino] ethyl) amino) naphthalene-1-sulphonic acid (IAEDANS) as donor with fluorescein as acceptor, and 5-(2-aminoethylamino) naphthalene-1-sulfonic acid (EDANS) as donor with 4-(4-dimethylaminophenylazo)benzoic acid (DABCYL) as acceptor.

In yet a still further embodiment, the donor and acceptor fluorophore can be of the same chemical structure and the transglycosylase product can be detected by fluorescence depolarization or electron spin resonance. Fluorescence depolarization is a technique in which a fluorophore, such as pyrene, is excited with polarized light. The fluorescence emitted will be polarized to a degree that is inversely related to the amount of Brownian motion which occurs between the interval of light absorption and emission. The amount of polarization is then a measure of the size of the molecule to which the fluorescence probe is bound. In solution, the fluorophores (such as PYT), will be rapidly moving and rotating, and thus little or no polarization of fluorescence will be observed. On the other hand, if the fluorescently labelled complex will be rotating and moving relatively slowly in solution. The fluorophore will emit polarized light because it is now bound to a larger structure which is not tumbling very rapidly in solution. This technique is particularly useful in cases where fluorescence intensity change might not be observable. The degree of polarization is measured by standard methods, such as with a commercially available fluorimeter having polarizing filters. Detection of product by shifts in the wavelengths of absorption or emission may also be possible if the environment of the fluorophore changes substantially upon formation of coupled product.

Furthermore, in another embodiment, the instant invention uses a singly labeled substrate analog containing a chromophore for evaluating the product length distribution as a function of time.

Reactions can be quenched and the products separated by affinity capillary electrophoresis or HPLC. The product length distributions can be evaluated to determine if the enzymes are processive or distributive vis-a-vis product formation.

The assay can be run using two differentially labeled substrate analogs or a singly labeled substrate depending on the question being addressed. Singly labeled substrates containing chromophores are most suitable if the product length distribution is to be determined or if the acceptors in the reaction mixture are polymeric or bound to a solid support or surface. Differentially labeled substrates provide for different assay formats, either affinity capture with radiometric, fluorometric, or colorimetric detection of product or a FRET-based assay for continuous monitoring of product. An affinity capture assay with radiometric detection can be formatted for use with scintillation proximity beads or plates. An affinity capture assay with fluorometric detection can be formatted to allow detection via changes in fluorescence polarization.

The assay can be carried out with impure sources of transglycosylase domain. A novel feature of the instant invention is that labels that are introduced permit detection of product regardless of the polymerization state of the product, either immediately or following separation of products from starting material.

5.3. Fluorophores and Isotopes

Many fluorophores are suitable for use in the instant invention, including, but not limited to: Alexa 350, Alexa 430, Alexa 488, Alexa 532, Alexa 546, Alexa 568, Alexa 594, AMCA, BODIPY 493/503, BODIPY FL, BODIPY FL Br2, BODIPY R6G, BODIPY 530/550, BODIPY TMR, BODIPY 558/568, BODIPY 564/570, BODIPY 576/589, BODIPY 581/591, BODIPY TR, BODIPY, Texas Red, BODIPY 630/650, BODIPY 650/665, Cascade Blue, Cascade Yellow, Cl-NERF, Dansyl, Dapoxyl dye, Dialkylaminocoumarin, 4',5'-Dichloro-2',7'-dimethoxy-fluorescein, 2',7'-Dichloro-fluorescein, DM-NERF, Eosin, Eosin F3S, Erythrosin, Fluorescein, Hydroxycoumarin, Isosulfan blue, Lissamine rhodamine B, Malachite green, Marina Blue dye, Methoxycoumarin, Naphthofluorescein, Oregon Green, Oregon Green 500, Oregon Green 514, Pacific Blue dye, Pyrene, Rhodamine 6G, Rhodamine Green dye, Rhodamine Red dye, Rhodol Green dye, 2',4',5',7'-Tetra-bromosulfone-fluorescein, Tetramethyl-rhodamine, Texas Red dye, and X-rhodamine.

Similarly, many isotopes, both radioisotopes and stable isotopes, are suitable as labels, including, but not limited to: $^{3}H$, $^{14}C$, $^{32}P$, $^{35}S$, and $^{125}I$. The choice of a particular isotope or label is dependent on numerous factors including stability, half life, the sensitivity required and inherent difficulties associated with a particular choice.

6. EXAMPLES

The following procedures are provided as non-limiting illustrations of preferred embodiments of the invention.

6.1. Method of Synthesis, Assembly, or Process

One embodiment of the assay involves the production of Lipid II substrate analogs by chemo-enzymatic synthesis. Two Lipid I substrate analogs are synthesized chemically as disclosed (WO99/38958, supra), one of which contains a biotin label or another "handle" or binding ligand that permits detection. The Lipid I substrate analogs are separately converted to the corresponding Lipid II analogs by MurG-catalyzed transfer of N-acetyl glucosamine. The GlcNAc utilized for transfer to the non-biotinylated Lipid I substrate is radiolabeled. Following conversion to product, the MurG is inactivated and the Lipid II substrate analogs are combined and treated with a source of transglycosylase. The reaction mixture is filtered over an avidin coated support (or other solid support with affinity for the handle) and the radioisotope retained on the support are counted to detect product. Compounds that inhibit product formation are identified by a reduction in the number of counts bound to the solid support. Coupled products of any length can be detected.

6.2. Alternate Method of Synthesis, Assembly, or Process

In another embodiment of the assay, two Lipid I substrate analogs are synthesized chemically as disclosed except that each analog contains a different fluorophore attached to the lysine side chain. These fluorophores are selected to have overlapping emission/excitation bands and therefore to be useful as donor-acceptor pairs for fluorescence energy transfer applications. The labeled Lipid I substrate analogs are separately converted to the corresponding Lipid II analogs by MurG catalyzed transfer of N-acetyl glucosamine. Conversion to product is detected by an increase in emission of the acceptor when the sample is irradiated at the excitation wavelength of the donor, or alternatively by quenching of the donor fluorescence by non-radiative energy transfer to the acceptor. These FRET-based assays permit continuous detection of product as a function of time and can be formatted for use with plate readers or for use with cuvettes and a fluorimeter.

Alternatively, a Lipid I substrate analog containing a biotin label is converted to a biotinylated Lipid H analog by treatment with UDP-GlcNAc in the presence of MurG. A second Lipid I substrate analog containing a fluorophore is converted to a fluorophorylated Lipid II analog by treatment with UDP-GlcNAc in the presence of MurG. The Lipid II analogs are combined and treated with a source of transglycosylase. The reactions are then transferred to a plate containing avidin or streptavidin-coated wells or beads. Fluorescently-labeled product that binds to the beads can be detected by monitoring changes in fluorescent polarization or anisotropy compared to the fluorophorylated Lipid II molecule itself. Alternatively, the transglycosylase can be added to the wells containing biotin-bound Lipid II and soluble fluorescent Lipid II and product formation detected continuously by monitoring changes in fluorescence polarization.

6.3. Another Method of Synthesis, Assembly, or Process

In yet another embodiment of the assay, the Lipid I substrate analog is synthesized chemically as disclosed except that a chromophore is attached to the lysine side chain. The substrate analog is converted to a Lipid II substrate analog by MurG-catalyzed transfer of N-acetyl glucosamine. Subsequently, transglycosylase is added to the Lipid II analog. The reaction is quenched at intervals and aliquots of the reaction mixtures are subjected to analyses by affinity capillary electrophoresis (ACE) or high-pressure liquid chromatography (HPLC). Different products will migrate at different rates in an ACE apparatus or through an appropriate HPLC column. The peaks will be analyzed to determine the concentration of product (using the chromophore for quantification) and the length distribution (e.g., by interfacing the HPLC column with a mass spectrometer such as an electrospray mass spectrometer).

6.4. Alternate Method of Synthesis, Assembly, or Process

In yet a further embodiment of the assay, Lipid II molecules that are differentially labeled with fluorophores are produced by isolating UDP-MurNAc pentapeptide and labeling the lysine with the appropriate fluorophores and then converting the molecules in situ to Lipid H by the action of MraY and MurG in particulate membrane preparations. The fluorescently labeled Lipid II molecules are produced with shorter lipid chains by adding appropriate lipid phosphates to the membrane preparations as determined by the length accepted by MraY. The fluorescently labeled molecules are isolated and then used in a FRET-based assay.

6.5. Alternate Method of Synthesis, Assembly, or Process

The same type of procedure for making. Lipid II molecules labeled with biotin can be used as above. The biotinylated Lipid II molecules can be used with either radiolabled Lipid II molecules or fluorescently labeled Lipid II molecules depending on the detection method desired (radiometric or fluorescence polarization or anisotropy). In yet another embodiment of the invention a luminescent label can be used instead of a fluorescent label. In this situation light is emitted from a donor molecule such as luciferin as a result of a redox reaction catalyzed by the enzyme luciferase. Generation of chemiluminescence can be also provided upon reaction of amines or an amine moiety with 2,2-bipyridine ruthinium, 1-amino-3-anthryl-(9)-propane, or by other means known in the art as disclosed for example in the U.S. Pat. No. 5,846,485.

Thus, the term light-emitting label as used hereinafter, in general, refers to any label or indicator, which emits fluorescent. luminiscent, evanescent light, or chemoluminescent ligh.

6.6. Assay of Transglycosylase-catalyzed Lipid II Analog Coupling to Peptidoglycan Polymer Product In another embodiment, a biotin-labeled Lipid II analog is produced as above, in Examples 6.1, 6.2, 6.3, or 6.5, and purified over an avidin or streptavidin affinity column. The purified Lipid II analog is added to a membrane preparation containing transglycosylase activity and peptidoglycan polymers containing acceptor sites for Lipid II analogs. Following filtration to remove unincorporated biotin label, formation of peptidoglycan polymers containing biotin labels can be detected by reaction with fluorescently-labeled avidin or streptavidin or by colorimetric detection of enzyme-linked streptavidin or avidin; or by radiometric detection if the Lipid II substrate is radiolabeled as well as biotin-labeled.

6.7. Inhibition Assays

Inhibition of transglycosylase activity can be evaluated by adding increasing concentrations of inhibitor to a standardized transglycosylase assay and monitoring the change in the signal compared to the reaction in the absence of inhibitor. For example, when an affinity capture assay with radiometric detection is used, inhibition is detected as a decrease in the number of counts incorporated as a function of time at each different concentration of inhibitor. When an affinity capture assay with fluorometric detection is used, inhibition can be detected as a decrease in emission at the emission wavelength of the acceptor when the donor is excited, or a decrease in biotin-dependent signal, as described in Example 6.6, following filtration of unincorporated biotin.

This assay allows one skilled in the art to screen and identify transglycosylase inhibitory activity of known and unknown antibiotics affecting bacterial wall synthesis. Specifically they comprise vacomycin, teicoplanin, ramoplanin, paldimycin, DuP 721 and DuP 105, methicillin and gentamicin, oxazolidinones, A/16686, A/16686 factor A1, antibiotic A/16686 factor A2, antibiotic A/16686 factor A3, antibiotic A/16686 factor A'1, antibiotic A/16686 factor A'2, antibiotic A/16686 factor A'3, any of the derivatives thereof hydrogenated in the fatty acid chain, any aglycons thereof, and any mixture thereof. Nisin and other related members of this class of lanthocin antimicrobial peptides, including subtilin; epidermin; gallidermin; EpiD, EpiA, pep 5; epilancin K7; cinnamycin; duramycin, and ancovenin, as well as structural variants of these molecules produced by genetic engineering or by semisynthetic chemistry, are useful in the prevention or therapy of infections caused by antibiotic-resistant bacteria in humans and animals. Not only all presently known lantibiotics: nisin, nisin Z, subtilin, epidermin, gallidermin, pep 5, duramycin and duramycin B, cinnamycin, cinramycin, mersacidin, actagardine, AlaO-actagardine, monocarboxyamide actagardine, and ancovenin, but also other lantibiotics, e.g., natural or synthetic peptides which contain the lanthio amino acids lanthionine, beta-methyllanthionine, beta-dimethyllanthionine, dehydroalanine and betaB-methyldehydroalanine are suitable. However, any properly selected amino acid residue can conservatively substite in existing peptide antibiotics. These include basic amino acids: lysine (Lys), arginine (Arg), histidine (His); acidic amino acids: aspartic acid (Asp), glutamic acid (Glu), asparagine (Asn), glutamine (Gln). Furthermore, other antibiotics with supposedly unrelated or related mechanisms of action can be screened further to reveal specific transglycosylase acitivity and/or binding/interferring activity to any of substrates of the present invention and to identify lead compounds with potential commercial utility. Non-limiting examples of such drugs include: Acedapsone; Acetosulfone Sodium; Alamecin; Alexidine; Amdinocillin; Amdinocillin Pivoxil; Amicycline; Amifloxacin; Amifloxacin Mesylate; Amikacin; Amikacin Sulfate; Aminosalicylic acid; Aminosalicylate sodium; Amoxicillin; Amphomycin; Ampicillin; Ampicillin Sodium; Apalcillin Sodium; Apramycin; Aspartocin; Astromicin Sulfate; Avilamycin; Avoparcin; Azithromycin; Azlocillin; Azlocillin Sodium; Bacampicillin Hydrochloride; Bacitracin; Bacitracin Methylene Disalicylate; Bacitracin Zinc; Bambermycins; Benzoylpas Calcium; Berythromycin; Betamicin Sulfate; Biapenem; Biniramycin; Biphenamine Hydrochloride; Bispyrithione Magsulfex; Butikacin; Butirosin Sulfate; Capreomycin Sulfate; Carbadox; Carbenicillin Disodium; Carbenicillin Indanyl Sodium; Carbenicillin Phenyl Sodium; Carbenicillin Potassium; Carumonam Sodium; Cefaclor; Cefadroxil; Cefamandole; Cefamandole Nafate; Cefamandole Sodium; Cefaparole; Cefatrizine; Cefazaflur Sodium; Cefazolin; Cefazolin Sodium; Cefbuperazone; Cefdinir; Cefepime; Cefepime Hydrochloride; Cefetecol; Cefixime; Cefmenoxime Hydrochloride; Cefmetazole; Cefmetazole Sodium; Cefonicid Monosodium; Cefonicid Sodium; Cefoperazone Sodium; Ceforanide; Cefotaxime Sodium; Cefotetan; Cefotetan Disodium; Cefotiam Hydrochloride; Cefoxitin; Cefoxitin Sodium; Cefpimizole; Cefpimizole Sodium; Cefpiramide; Cefpiramide Sodium; Cefpirome Sulfate; Cefpodoxime Proxetil; Cefprozil; Cefroxadine; Cefsulodin Sodium; Ceftazidime; Ceftibuten; Ceftizoxime Sodium; Ceftriaxone Sodium; Cefuroxime; Cefuroxime Axetil; Cefuroxime Pivoxetil; Cefuroxime Sodium; Cephacetrile Sodium; Cephalexin; Cephalexin Hydrochloride; Cephaloglycin; Cephaloridine; Cephalothin Sodium; Cephapirin Sodium; Cephradine; Cetocycline Hydrochloride; Cetophenicol; Chloramphenicol; Chloramphenicol Palmitate; Chloramphenicol Pantothenate Complex; Chloramphenicol Sodium Succinate; Chlorhexidine Phosphanilate; Chloroxylenol; Chlortetracycline Bisulfate; Chlortetracycline Hydrochloride; Cinoxacin; Ciprofloxacin; Ciprofloxacin Hydrochloride; Cirolemycin; Clarithromycin; Clinafloxacin Hydrochloride; Clindamycin; Clindamycin Hydrochloride; Clindamycin Palmitate Hydrochloride; Clindamycin Phosphate; Clofazimine; Cloxacillin Benzathine; Cloxacillin Sodium; Cloxyquin; Colistimethate Sodium; Colistin Sulfate; Coumermycin; Coumermycin Sodium; Cyclacillin; Cycloserine; Dalfopristin; Dapsone; Daptomycin; Demeclocycline; Demeclocycline Hydrochloride; Demecycline; Denofungin; Diaveridine; Dicloxacillin; Dicloxacillin Sodium; Dihydrostreptomycin Sulfate; Dipyrithione; Dirithromycin; Doxycycline; Doxycycline Calcium; Doxycycline Fosfatex; Doxycycline Hyclate; Droxacin Sodium; Enoxacin; Epicillin; Epitetracycline Hydrochloride; Erythromycin; Erythromycin Acistrate; Erythromycin Estolate; Erythromycin Ethylsuccinate; Erythromycin Gluceptate; Erythromycin Lactobionate; Erythromycin Propionate; Erythromycin Stearate; Ethambutol Hydrochloride; Ethionamide; Fleroxacin; Floxacillin; Fludalanine; Flumequine; Fosfomycin; Fosfomycin Tromethamine; Fumoxicillin; Furazolium Chloride; Furazolium Tartrate; Fusidate Sodium; Fusidic Acid; Gentamicin Sulfate; Gloximonam; Glyphomicin A and B; Haloprogin; Hetacillin; Hetacillin Potassium; Hexedine; Ibafloxacin; Imipenem; Isoconazole; Isepamicin; Isoniazid; Josamycin; Kanamycin Sulfate; Kitasamycin; Levofuraltadone; Levopropylcillin Potassium; Lexithromycin; Lincomycin; Lincomycin Hydrochloride; Lomefloxacin; Lomefloxacin Hydrochloride; Lomefloxacin Mesylate; Loracarbef; Mafenide; Meclocycline; Meclocycline Sulfosalicylate; Megalomicin Potassium Phosphate; Mequidox; Meropenem; Methacycline; Methacycline Hydrochloride; Methenamine; Methenamine Hippurate; Methenamine Mandelate; Methicillin Sodium; Metioprim; Metronidazole Hydrochloride; Metronidazole Phosphate; Mezlocillin; Mezlocillin Sodium; Minocycline; Minocycline Hydrochloride; Mirincamycin Hydrochloride; Monensin; Monensin Sodiumr; Nafcillin Sodium; Nalidixate Sodium; Nalidixic Acid; Natainycin; Nebramycin; Neomycin Palmitate; Neomycin Sulfate; Neomycin Undecylenate; Netilmicin Sulfate; Neutramycin; Nifuiradene; Nifuraldezone; Nifuratel; Nifuratrone; Nifurdazil; Nifurimide; Nifiupirinol; Nifurquinazol; Nifurthiazole; Nitrocycline; Nitrofurantoin; Nitromide; Norfloxacin; Novobiocin Sodium; Ofloxacin; Onnetoprim; Oxacillin Sodium; Oximonam; Oximonam Sodium; Oxolinic Acid; Oxytetracycline; Oxytetracycline Calcium; Oxytetracycline Hydrochloride; Paldimycin; Parachlorophenol; Paulomycin; Pefloxacin; Pefloxacin Mesylate; Penamecillin; Penicillin G Benzathine; Penicillin G Potassium; Penicillin G Procaine; Penicillin G Sodium; Penicillin V; Penicillin V Benzathine; Penicillin V Hydrabamine; Penicillin V Potassium; Pentizidone Sodium; Phenyl Aminosalicylate; Piperacillin Sodium; Pirbenicillin Sodium; Piridicillin Sodium; Pirlimycin Hydrochloride; Pivampicillin Hydrochloride; Pivampicillin Pamoate; Pivampicillin Probenate; Polymyxin B Sulfate; Porfiromycin; Propikacin; Pyrazinamide; Pyrithione Zinc; Quindecamine Acetate; Quinupristin; Racephenicol; Ramoplanin; Ranimycin; Relomycin; Repromicin; Rifabutin; Rifametane; Rifamexil; Rifamide; Rifampin; Rifapentine; Rifaximin; Rolitetracycline; Rolitetracycline Nitrate; Rosaramicin; Rosaramicin Butyrate; Rosaramicin Propionate; Rosaramicin Sodium Phosphate; Rosaramicin Stearate; Rosoxacin; Roxarsone; Roxithromycin; SF-2288; Sancycline; Sanfetrinem Sodium; Sarmoxicillin; Sarpicillin; Scopafungin; Sisomicin; Sisomicin Sulfate; Sparfloxacin; Spectinomycin Hydrochloride; Spiramycin; Stallimycin Hydrochloride; Steffimycin; Streptomycin Sulfate; Streptonicozid; Sulfabenz; Sulfabenzamide; Sulfacetamide; Sulfacetamide Sodium; Sulfacytine; Sulfadiazine; Sulfadiazine Sodium; Sulfadoxine; Sulfalene; Sulfamerazine; Sulfameter; Sulfamethazine; Sulfamethizole; Sulfamethoxazole; Sulfamonomethoxine; Sulfamoxole; Sulfanilate Zinc; Sulfanitran; Sulfasalazine; Sulfasomizole; Sulfathiazole; Sulfazamet; Sulfisoxazole; Sulfisoxazole Acetyl; Sulfisboxazole Diolamine; Sulfomyxin; Sulopenem; Sultamricillin; Suncillin Sodium; Talampicillin Hydrochloride; Teicoplanin; Temafloxacin Hydrochloride; Temocillin; Tetracycline; Tetracycline Hydrochloride; Tetracycline Phosphate Complex; Tetroxoprim; Thiamphenicol; Thiphencillin Potassium; Ticarcillin Cresyl Sodium; Ticarcillin Disodium; Ticarcillin Monosodium; Ticlatone; Tiodonium Chloride; Tobramycin; Tobramycin Sulfate; Tosufloxacin; Trimethoprim; Trimethoprim Sulfate; Trisulfapyrimidines; Troleandomycin; Trospectomycin Sulfate; Vancomycin; Vancomycin Hydrochloride; desleucyl-Vancomycin (desleucyl-V); chlorobiphenyl-Vancomycin (CBP-V), chlorobiphenyl-desleucyl-Vancomycin (CBP-desleucyl-V); Virginiamycin; Zorbamycin, and derivatives thereof.

Figure 8:
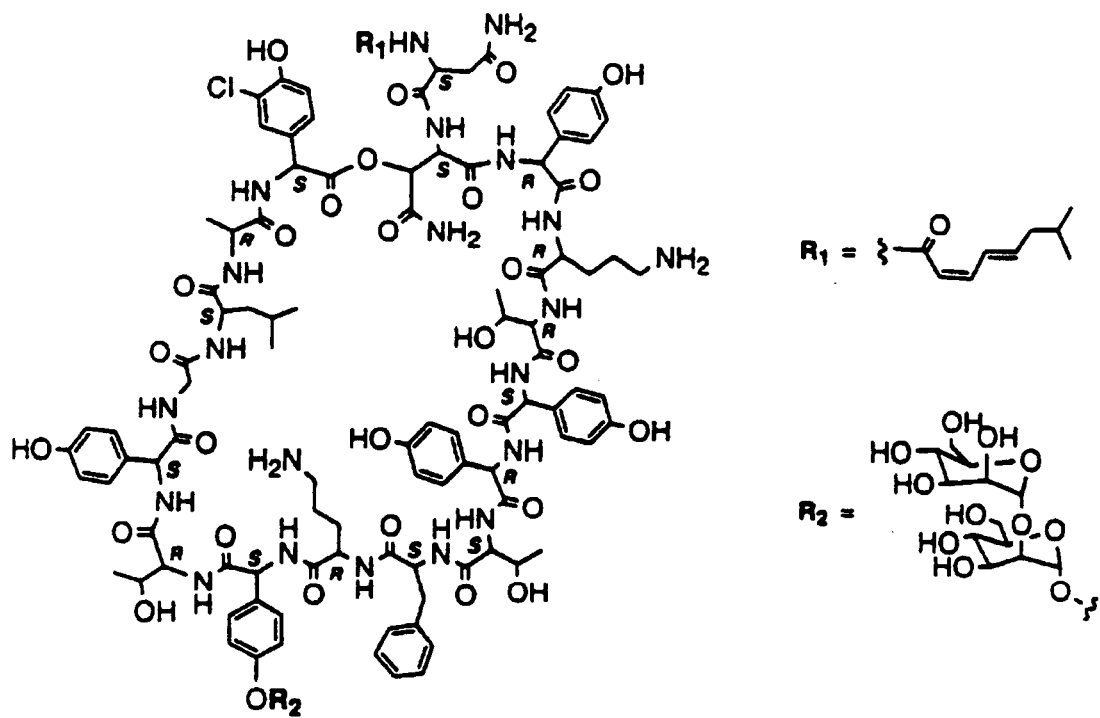
FIG. 8 illustrates ramoplanin (factor A2) molecule.
Figure 9:
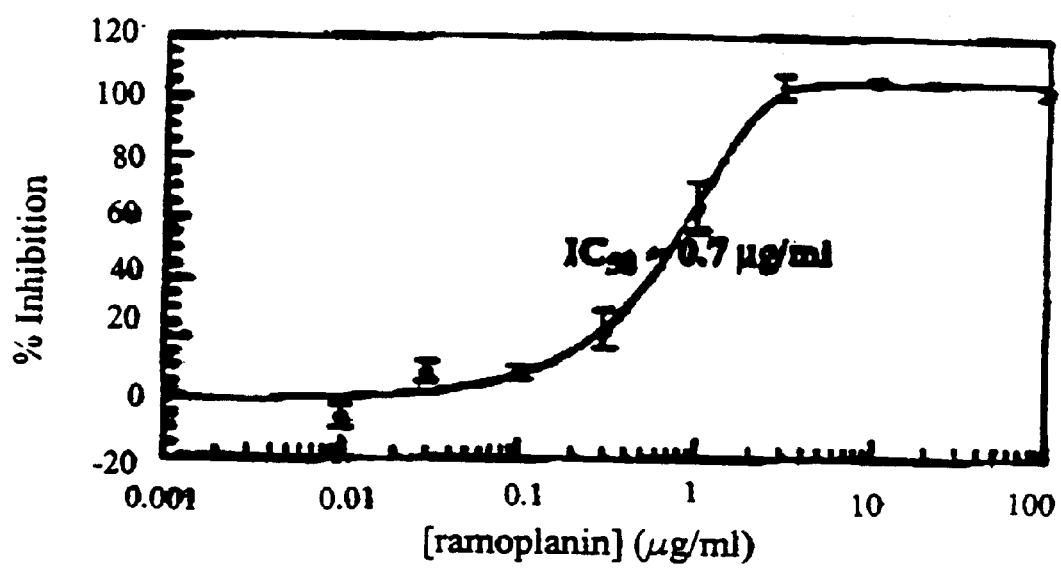
FIG. 9 illustrates inhibition radiolabeled Lipid II polymerization with serial dilutions of ramoplanin.
Figure 10:
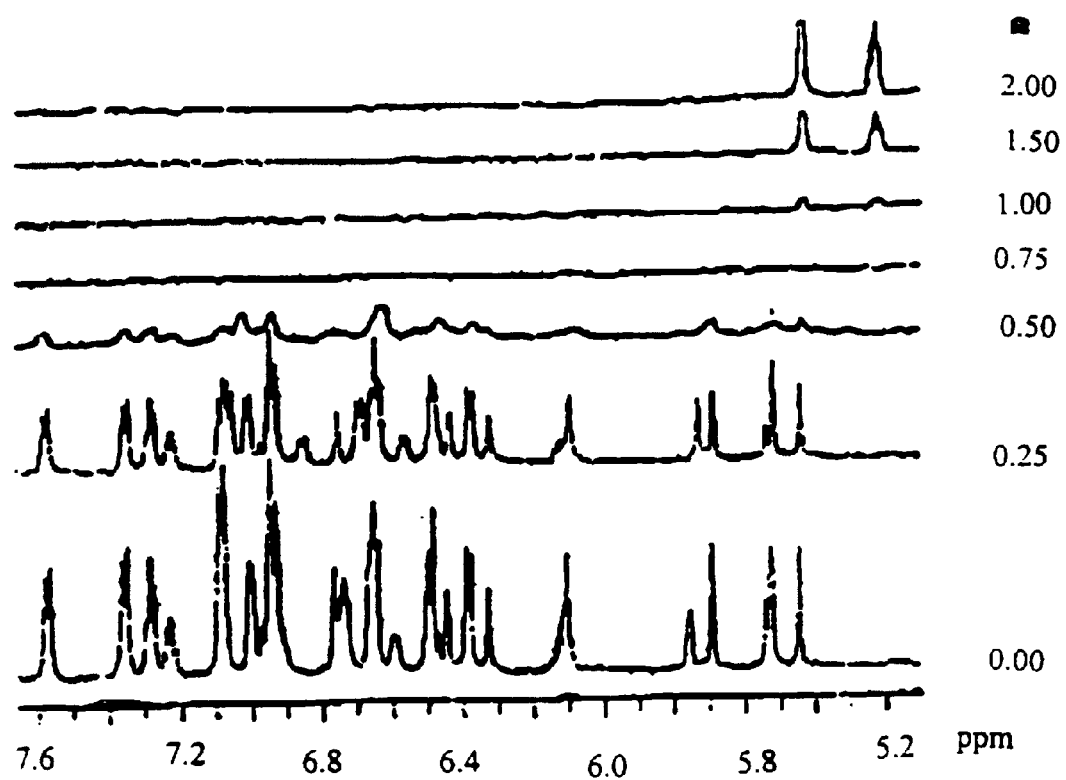
FIG. 10 illustrates NMR spectra of ramoplanin with compound 2.
Figure 11:
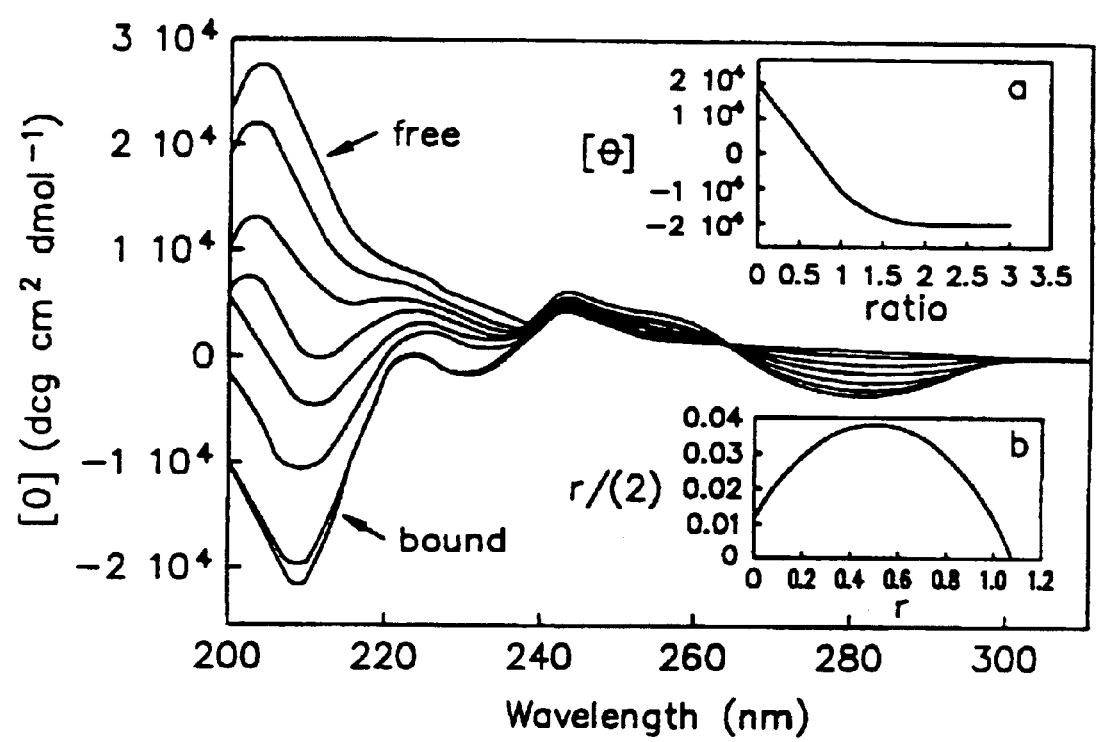
FIG. 11 illustrates CD spectra of ramoplanin upon titration with 2.
Figure 12:
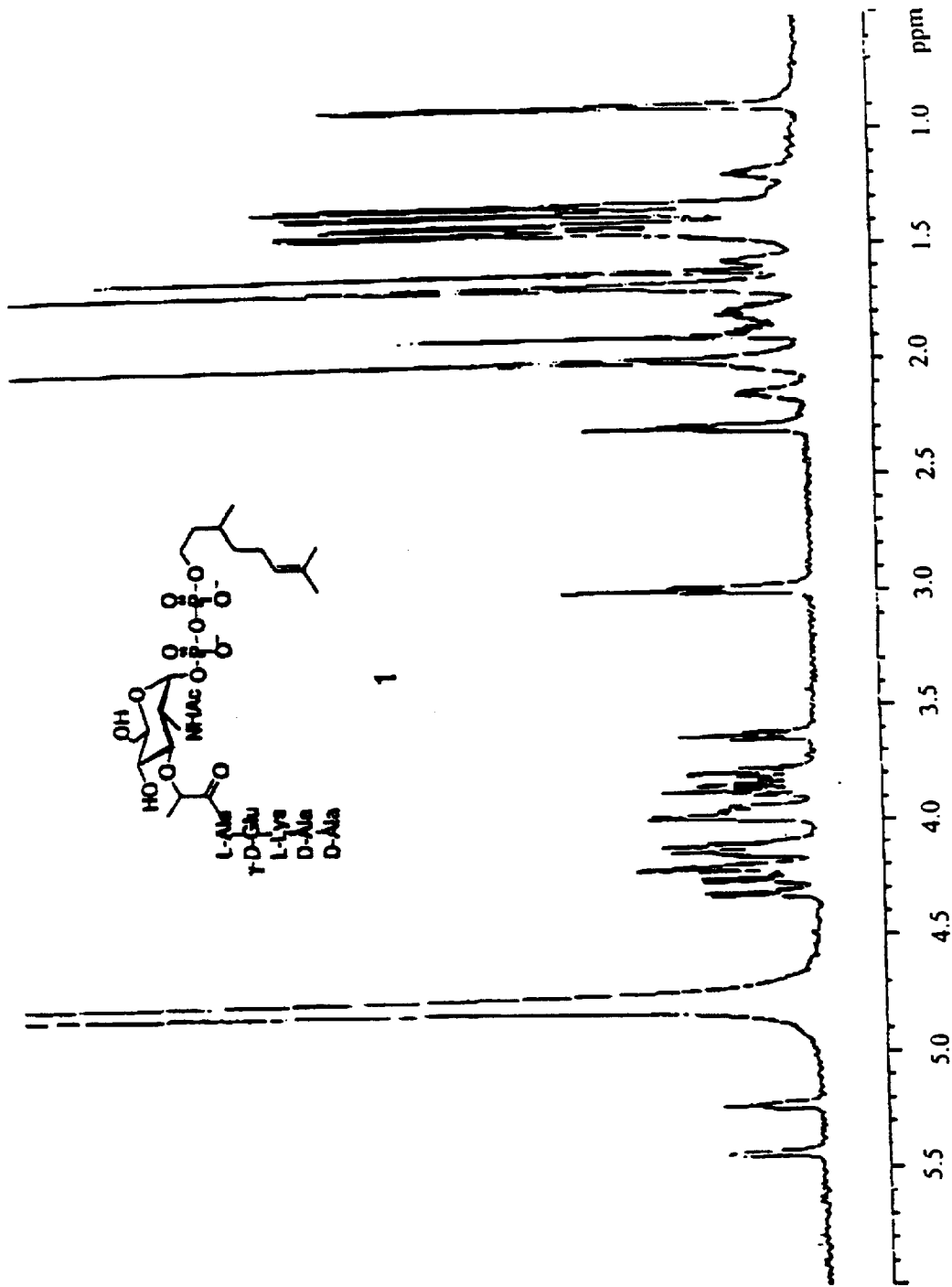
FIG. 12 illustrates NMR spectra with Lipid I or compound 1.
Figure 13:
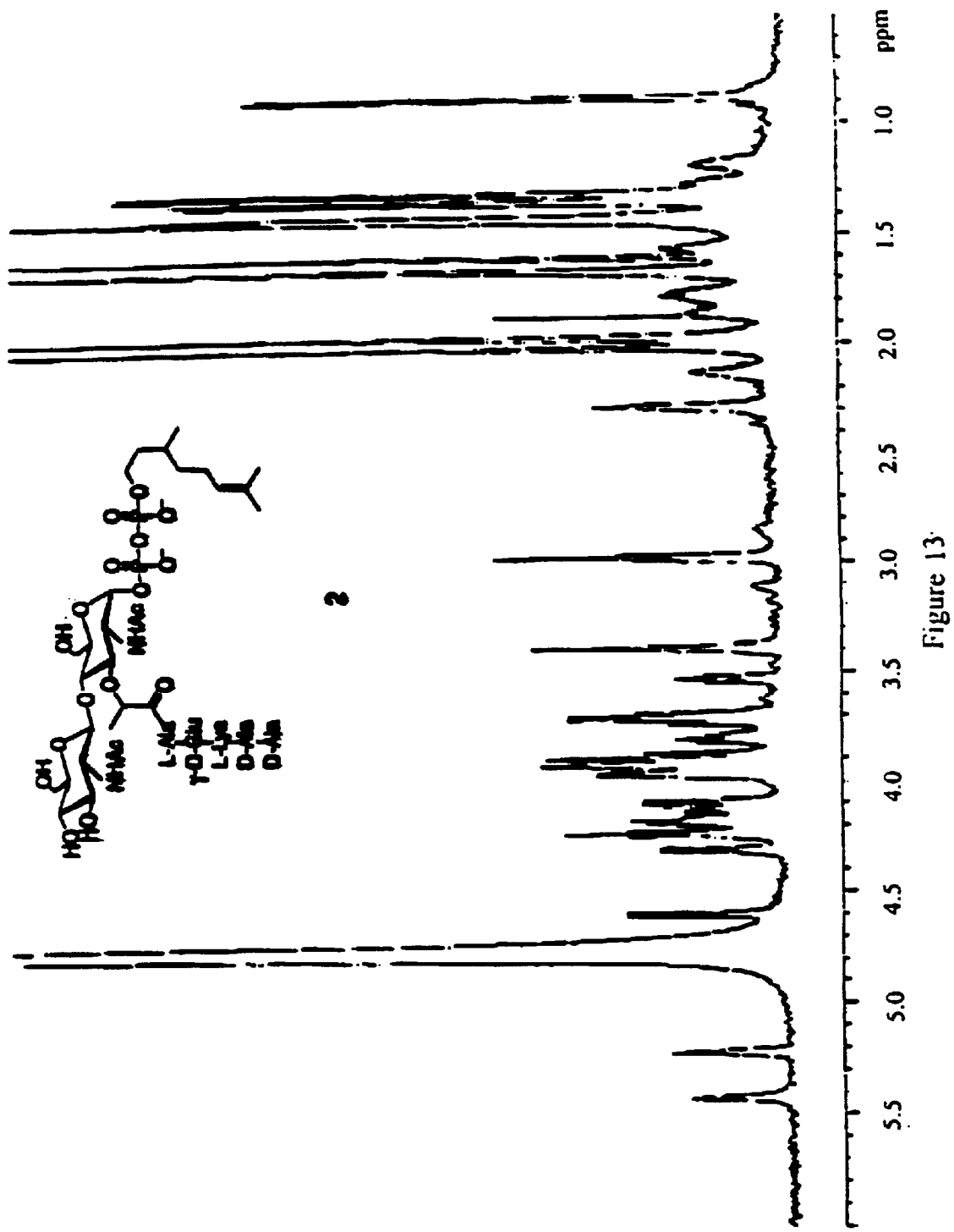
FIG. 13 illustrates NMR spectra with Lipid II or compound 2.

Ramoplanin (FIG. 8) is a cyclic glycolipodepsipeptide antibiotic that kills gram positive bacteria by inhibiting cell wall biosynthesis. Ramoplanin blocks the conversion of Lipid I to Lipid II, a reaction that is catalyzed by the intracellular GlcNAc transferase. MurG. It is proposed that ramoplanin inhibits MurG by complexing Lipid I, which prevents it from being utilized as a substrate. Unexpectedly ramoplanin is shown by this inventor to inhibit the polymerization of Lipid II; therefore another mechanism is discovered by which ramoplanin can kill bacterial cells through inhibition of the transglycosylation step of peptidoglycan synthesis. Using a synthetic analogue of Lipid II, the evidence is presented that enzyme inhibition by ramoplanin involves substrate binding. Unexpectedly, the ramoplanin complexes are found to self-associate to form observable fibrils. The mechanism of action of ramoplanin has been investigated in the past in permeabilized bacterial cells and membrane preparations by following the incorporation of radiolabel from a precursor into various intermediates along the pathway to peptidoglycan. A limitation of these assays is that if one enzymatic step is blocked, then no information can be obtained about subsequent steps. Thus, because ramoplanin prevents the formation of Lipid II, it is not possible to determine whether it also inhibits the polymerization of Lipid H. Herein the ability of ramoplanin to block Lipid II polymerization is investigated using a modified membrane assay in which the transglycosylases are selectively inhibited to permit the build-up of radiolabeled Lipid II. Following removal of the inhibitor, peptidoglycan synthesis commences. The effect of ramoplanin on Lipid II polymerization is evaluated by monitoring the amount of radioactive peptidoglycan formed in the presence of increasing concentrations of ramoplanin. Ramoplanin blocks the polymerization of Lipid II and thus it is discovered as being an inhibitor of the transglycosylation step of peptidoglycan synthesis (FIG. 9). Ramoplanin was proposed to act by completing substrates required for peptidoglycan synthesist. Unfortunately, the prior art difficulties in isolating Lipid intermediates from bacterial cells have hindered studies of their interactions with ramoplanin. Moreover, the natural lipid intermediates contain a long 55 carbon polyprenol chain that renders them insoluble in water, and thus difficult to use in biophysical studies of complex formation-Using purified MurG, it is now possible to construct the Lipid II analogue. Compound 2 is identical to natural Lipid II except that the 55 carbon chain is replaced with a ten carbon unit so that the compound is freely water soluble. While preferred composition is operable in aqueous solvent or milieu, media composed entirely or partially of organic solvents are equally suitable. The non-limiting examples of solvents include organic solvents that are equally suitable including but not limited to benzene, toluene, xylene, cyclohexane, hexane, ligroin, methyl isobutyl ketone, methyl acetate, ethyl acetate, butyl acetate, methyl CELLOSOLVE, ethyl CELLOSOLVE, butyl CELLOSOLVE, diethylene glycol monobutyl ether, diethylene glycol monobutyl ether acetate, methanol, ethanol, n-propyl alcohol, isopropyl alcohol, n-hexanol, cyclohexanol, and 2-ethylhexyl alcohol The ability of ramoplanin to interact with 2 is investigated by NMR (FIG. 10). Unexpectedly, titration of ramoplanin with compound 2 caused the ramoplanin signals to disappear. Resonances for free 2 began to appear at a 1:1 ramoplanin:2 ratio. The disappearance of the ramoplanin resonances connotes a change in relaxation properties consistent with the formation of a high molecular weight species. A striking increase in the viscosity of the ramoplanin samples is evident upon the addition of compound 2. In addition, electron micrographs of the ramoplanin complexes show long fibrils (not shown). Thus, ramoplanin undergoes a ligand-induced polymerization process in the presence of 2. Ligand-induced polymerization of ramoplanin complexes implies a conformational change in ramoplanin. Therefore, one would expect a significant change in the far UV CD spectrum of ramoplanin upon adding 2. In fact, the CD spectrum for ramoplanin changes dramatically upon titration with 2 (FIG. 11). The appearance of a minimum at ~210 nm is consistent with a model in which assembly into fibrils is mediated by hydrogen bonds between amides in the ramoplanin complexes, and is all likelihood related to the unusual pattern of D and L amino acids in the molecule. The chance in ellipticity of ramoplanin upon adding 2 levels off at a ratio of approximately 1:1 (FIG. 11, inset a), the same ratio at which signals for free 2 begin to show up in the NMR titrations. Hence, the apparent stoichiometry for complex formation is 1:1, however, Scatchard analysis of the CD data produces a concave, down curve (FIG. 11. inset b), which is consistent with a ligand-dependent polymerization process. The IC50 for inhibition of Lipid II polymerization indicates that the apparent stoichiometry for ramoplanin complex formation at membrane interfaces is also 1:1. Thus, ramoplanin is an inhibitor of the transglycosylation step of peptidoglycan synthesis. Ramoplanin binds to a synthetic analogue of Lipid II, indicating that enzyme inhibition involves substrate binding. Unexpectedly, substrate binding induces ramoplanin polymerization. Thus, this invention makes possible the use of instant soluble Lipid analogues to characterize the mechanisms of action of other antibiotics interacting with Lipid I and/or Lipid II substrates.

6.8. Use of Alternate Separation/Detection Media

Avidin or streptavidin coated microparticles, avidin or streptavidin coated membrane filters, and avidin or streptavidin coated glass fibers, and avidin or strepatavidin coated wells can be used. Scintillant-entrapping coated particles permit the use of scintillation proximity assays. Avidin or streptavidin coated plates and appropriate fluorescent plate readers permit the use of fluorescence polarization or anisotropy assays. Other types of fluorescent plate readers permit the use of FRET-based assays.

6.9. General Methods

Methods for synthesizing Lipid I substrate analogs are reported in WO 99/38958 which is incorporated herein by way of reference.

6.10. Synthesis and Purification of Lipid II Analogs that Contain Biotin and Validation of Their Use as Substrates for Transglycosylase Native Lipid II derivatized with biotin is synthesized from UDP-GlucNAc and UDP-MurNAc-pentapeptide (conjugated with biotin on the amino group of lysine), using bacterial membrane preparations. Biotin can be attached by a crosslinking agent or linker. Linker can be selected from any of following: ethylene glycol dimethacrylate, divinyl benzene, trimethylol propane trimethacrylate, N,N'methylene-bis-acrylamide, aryl azides, fluorinated aryl azides, and benzophenones like iodoacetamide or maleimide derivatives of benzophenone (BPIA and BPM). Other linkers which can be employed are N,N-dicyclohexylcarbodiimide, 1-ethyl-3(3-dimethyl aminopropyl)carbodiimide hydrochloride and 1-cyclohexyl-3-(2-morpholinyl-(4)-ethylcarbodiimide)methyl-p-toluene sulfonate. Other crosslinking or bifunctional coupling linker agent which can be utilized are compounds having two or more of the following reactive groups: azo, sulfonic acid, fluoro groups activated by nitro groups, azide, imine and reactive chloro groups having proper suitable structure. These reactive groups are capable of reacting with the primary amino, sulfylhydryl, carboxylic, hydroxyl and phenolic groups are suitable. Representative of such other coupling agents or linkers are bis-diazobenzidine, disulfonic acid, tetraazo-p-phenylenediamine, difluorodinitrobenzene, difluorodinitrophenylsulfone, toluene diisocyanate, cyanuric chloride and dichlorotriazine.

The typical yield of biosynthesized biotinylated Lipid II is 70%–80% of added UDP-GlcNAc. Biotinylated Lipid II is extracted and purified using solid support (Softlink avidin chromatography resin, Promega, Madison Wis.) as outlined in FIG. 6. Purification of biotinylated Lipid II is facilitated, thus providing enhanced yields of Lipid II, 64% to 91% of bound biotin-Lipid II eluting to give overall recoveries of 50% to 78%.

Figure 7:
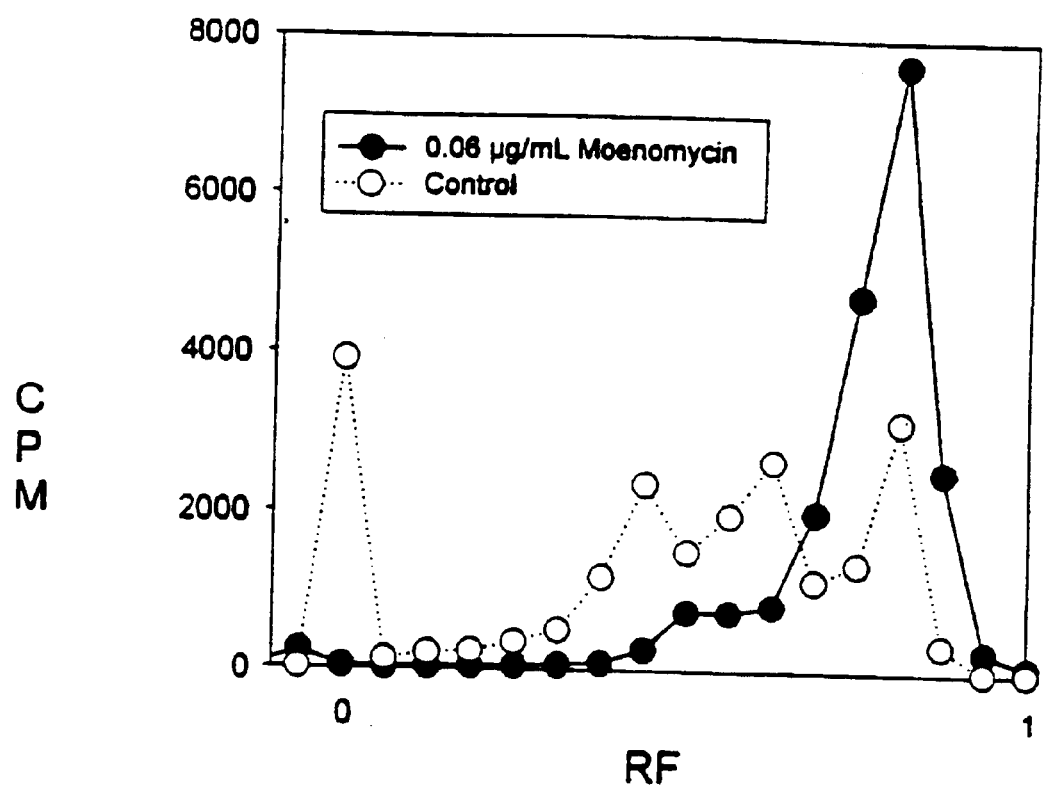
FIG. 7 illustrates the separation of reaction products from the transglycosylase reaction assayed in the absence (solid symbols) and presence (gray symbols) of moenomycin.

FIG. 7 discloses in vitro polymerization of biotinylated-[$^{14}$C]-Lipid II accomplished by incubation with bacterial membrane protein, and product is detected by ascending chromatography in isobutyric acid:1M NH4OH (5:3). The product is the result of enzymatic conversion of biotinylated-[$^{14}$C]-Lipid II into peptidoglycan by transglycosylase, since product does not migrate, and formation is inhibited by the presence of the known transglycosylase inhibitor moenomycin (See, FIG. 7). These data show that biotinylated substrates are recognized by transglycosylase, and can be used in conversion to peptidoglycan.

In FIG. 7, biotinylated Lipid II serves as a substrate for transglycosylase present in bacterial membranes. Control: incubation of bacterial membranes with biotinylated Lipid II, which is also labeled with [$^{14}$C] GlucNAc, demonstrates conversion of substrate into peptidoglycan product that remains at the origin (Rf=0). The curve labeled "0.06 µg/ml Moenomycin" illustrates incubation of bacterial membranes with biotinylated Lipid II, which is also labeled with [$^{14}$C]-GlucNAc, in the presence of the known transglycosylase inhibitor moenomycin, which inhibits formation of peptidoglycan. Thus, the data demonstrate that the product obtained in the absence of moenomycin is peptidoglycan. It is thus clear that any other bacterial cell wall inhibitor can be equally screened.

Separation of peptidoglycan (poly(peptidosaccharide), which incorporated biotinylated-cell wall disaccharide, from unincorporated biotinylated Lipid II substrate analog, allows detection of enzyme product by measuring the amount of biotin incorporated into peptidoglycan. This is accomplished using avidin (or derivatives thereof) or strepavidin (or derivatives thereof) conjugates containing fluorescent reporters (e.g., fluorescein, R-phycoerythrin, rhodamine, Oregon green, etc.), enzyme reporters (e.g., peroxidase, alkaline phosphatase, β-galactosidase, etc.), radiolabel, or other reporter units. Any functional group attached to native Lipid II, or synthetic analogs thereof, which allows processing of Lipid II or its analogs by transglycosylase, and also serves as reporter can thus be used to generate a signal indicative of transglycosylase activity. Such assays are performed in solution, or, alternatively, on solid supports in a moist environment, and processed to separate unincorporated material. Separation of substrate from product is accomplished by trapping peptidoglycan, with or with out precipitation with a denaturant, on filters, or by differential centrifugation, or other physical or chemical separation methods (e.g., extraction and phase separations).

Sources of transglycosylase include a) bacterial membranes prepared following lysis of bacterial cells, b) normal or regenerating bacterial spheroplasts or protoplasts from which the cell wall has been removed, c) bacterial cells permeabilized with organic solvents, d) mutant bacterial cells containing defects in the outer membrane that render them permeable, or e) transglycosylase enriched or purified from bacterial membranes or lysates. Bacterial sources include laboratory strains, clinical isolates, and derivatives thereof which have been genetically engineered to express specific transglycosylases in membrane bound or soluble form.

Alternatively, Lipid II, or analogs thereof, are derivatized with chemical groups which function directly as reporters, to yield additional substrates for transglycosylase enzymatic activity. Such reporters include fluorescent chromophores, hapten conjugates, or groups amenable to direct radiolabeling, for example, groups containing phenolic hydroxyl groups for iodination with radioactive iodine. Appropriate fluorescent groups allow for monitoring the reaction by changes in fluorescence properties, for example, shifts in wavelength or increases or decreases in intensity.

Covalent attachment of hapten groups, including, but not limited to dinitrophenol, to Lipid II or analogs thereof permit separation of product using antibody to the hapten structure as an alternative to aviden-biotin. Lipid II conjugated to a reporter enzyme can also be used for product detection in an ELISA format.

The purpose of the above description and examples is to illustrate some embodiments of the present invention without implying any limitation. It will be apparent to those of skill in the art, in light of this teaching, that various modifications and variations may be made to the compositions and methods in the present invention to generate additional embodiments without departing from the spirit or scope of the invention. Accordingly, it is to be understood that the drawings and descriptions in this disclosure are proffered to facilitate comprehension of the invention and should not be construed to limit the scope thereof.

What is claimed is:

1. A composition comprising a compound having the formula (I):

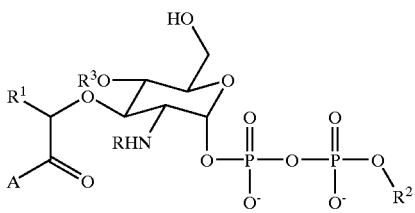

(I)

in which R is an acetyl group, $R^1$ is a methyl group, $R^2$ is a substituted or unsubstituted alkyl or alkenyl group comprising at least five carbon atoms, $R^3$ is a deoxyacylamino sugar, and A is a substituted or unsubstituted amino acid residue or a peptide comprising at least two substituted or unsubstituted amino acid residues.

2. The compound of claim 1 wherein said amino acid residue or peptide is synthetic or naturally-occurring.

3. The compound of claim 2 wherein $R^2$ comprises ether lipids, glycolipids, steroids, or at least one isoprene unit.

4. The compound of claim 2 in which $R^2$ comprises an isoprene unit comprising about 55 carbon atoms.

5. The compound of claim 4 in which $R^2$ comprises an isoprene unit comprising about 25 carbon atoms.

6. The compound of claim 2 in which $R^3$ is selected from the group consisting of N-acetylglucosamine, N-acetylmuramine, N-acetylmannosamine, and N-acetylgalactosamine.

7. The compound of claim 2 in which $R^3$ is N-acetylmuramine.

8. The compound of claim 2 in which A is a pentapeptide.

9. The compound of claim 1 which is labeled with an isotope, chromophore, fluorophore, or an affinity label.

10. The compound of claim 9 wherein $R^3$ is labeled.

11. The compound of claim 9 wherein A is labeled.

12. The compound of claim 9 wherein A is a pentapeptide having the sequence L-Ala-γ-D-Glu-L-Lys-D-Ala-D-Ala.

13. The compound of claim 12 wherein said pentapeptide is labeled with a dansyl moiety.

14. The compound of claim 13 wherein said dansyl moiety is attached to the ε-lysine residue of said pentapeptide.

15. A composition comprising the compound having the formula (I):

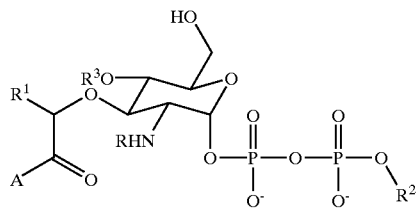

(I)

in which R is an acetyl group, $R^1$ is a methyl group, $R^2$ is a substituted or unsubstituted alkyl or alkenyl group comprising at least five carbon atoms, $R^3$ is N-acetymuramine, and A is a synthetic or naturally-occurring pentapeptide having the sequence L-Ala-γ-D-Glu-L-Lys-D-Ala-D-Ala, wherein said pentapeptide is labeled with a dansyl moiety.

16. The compound of claim 15 wherein said dansy moiety is attached to the ε-lysine residue of said pentapeptide.

* * * * *